(12) United States Patent
Sgroi, Jr.

(10) Patent No.: US 10,765,428 B2
(45) Date of Patent: Sep. 8, 2020

(54) HERMETIC FORCE SENSORS FOR SURGICAL DEVICES

(71) Applicant: Covidien LP, Mansfield, MA (US)

(72) Inventor: Anthony Sgroi, Jr., Wallingford, CT (US)

(73) Assignee: COVIDIEN LP, Mansfield, MA (US)

(*) Notice: Subject to any disclaimer, the term of this patent is extended or adjusted under 35 U.S.C. 154(b) by 436 days.

(21) Appl. No.: 15/666,021

(22) Filed: Aug. 1, 2017

(65) Prior Publication Data

US 2018/0042610 A1 Feb. 15, 2018

Related U.S. Application Data

(60) Provisional application No. 62/375,043, filed on Aug. 15, 2016.

(51) Int. Cl.
| | |
|---|---|
| *G01L 5/00* | (2006.01) |
| *A61B 17/072* | (2006.01) |
| *A61B 17/115* | (2006.01) |
| *A61B 17/068* | (2006.01) |
| *A61B 17/34* | (2006.01) |

(Continued)

(52) U.S. Cl.
CPC .... *A61B 17/07207* (2013.01); *A61B 17/0684* (2013.01); *A61B 17/1155* (2013.01); *A61B 17/3494* (2013.01); *G01L 5/0028* (2013.01); *A61B 2017/00017* (2013.01); *A61B 2017/0046* (2013.01); *A61B 2017/00367* (2013.01); *A61B 2017/00473* (2013.01); *A61B 2090/064* (2016.02)

(58) Field of Classification Search
CPC .......... A61B 17/07207; A61B 17/1155; A61B 17/0684; A61B 17/3494; A61B 2017/0046; A61B 2017/00473; A61B 2017/00017; A61B 2017/00367; A61B 2090/064; G01L 5/0028

See application file for complete search history.

(56) References Cited

U.S. PATENT DOCUMENTS

| | | | |
|---|---|---|---|
| 4,420,652 A | 12/1983 | Ikeno | |
| 4,672,418 A | 6/1987 | Moran et al. | |
| 5,041,943 A | 8/1991 | Ilardi et al. | |

(Continued)

FOREIGN PATENT DOCUMENTS

| | | |
|---|---|---|
| EP | 2959841 A1 | 12/2015 |
| WO | 2009-108214 A1 | 9/2009 |
| WO | 2010-022272 A1 | 2/2010 |

OTHER PUBLICATIONS

Extended European Search Report corresponding to counterpart European Patent Appln. No. EP 17 18 6271.7 dated Dec. 12, 2017.

*Primary Examiner* — Jonathan M Dunlap

(57) ABSTRACT

A force sensor includes a substrate, a plurality of sensing elements, and a plate. The substrate includes a central aperture extending along a longitudinal axis of the substrate, and has a proximal surface, a distal surface, a first side surface, a second side surface, a top surface, and a bottom surface. A recess is defined in at least one of the distal surface, the first side surface, the second side surface, the top surface, or the bottom surface of the substrate. The plurality of sensing elements are disposed within the recess, and the plate is disposed over the recess and mounted to the substrate to hermetically seal the plurality of sensing elements within the substrate.

20 Claims, 15 Drawing Sheets

(51) Int. Cl.
 *A61B 17/00* (2006.01)
 *A61B 90/00* (2016.01)

(56) References Cited

U.S. PATENT DOCUMENTS

| | | |
|---|---|---|
| 5,223,741 A | 6/1993 | Bechtel et al. |
| 5,280,413 A | 1/1994 | Pai |
| 5,497,290 A | 3/1996 | Fukui et al. |
| 5,940,279 A | 8/1999 | Gademann et al. |
| 6,320,128 B1 | 11/2001 | Glovatsky et al. |
| 6,351,194 B2 | 2/2002 | Takahashi et al. |
| 6,449,168 B1 | 9/2002 | Soderholm |
| 6,789,435 B2 * | 9/2004 | Hopkins ............... G01L 1/2243 177/211 |
| 6,794,587 B2 * | 9/2004 | Aumard ............... G01G 3/1412 177/211 |
| 7,898,074 B2 | 3/2011 | Eckhardt et al. |
| 8,354,587 B2 | 1/2013 | Tappel et al. |
| 8,666,505 B2 | 3/2014 | O'Brien et al. |
| 9,442,131 B2 | 9/2016 | Hazel et al. |
| 2007/0157734 A1 * | 7/2007 | Skwara .................. G01L 9/045 73/708 |
| 2013/0023917 A1 | 1/2013 | Cruz Hernandez et al. |
| 2016/0296234 A1 | 10/2016 | Richard et al. |
| 2016/0310134 A1 | 10/2016 | Contini et al. |
| 2017/0086879 A1 | 3/2017 | Williams |

\* cited by examiner

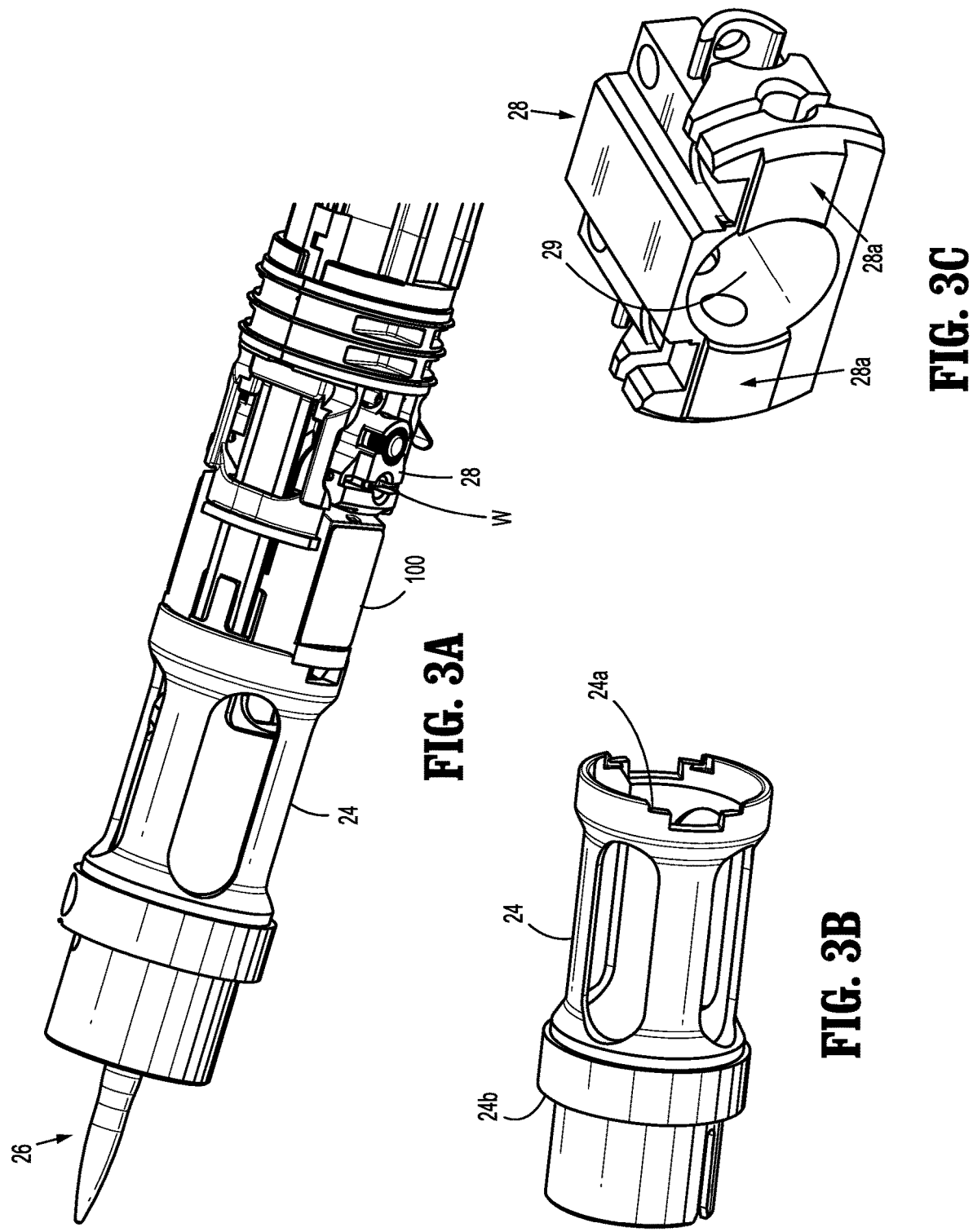

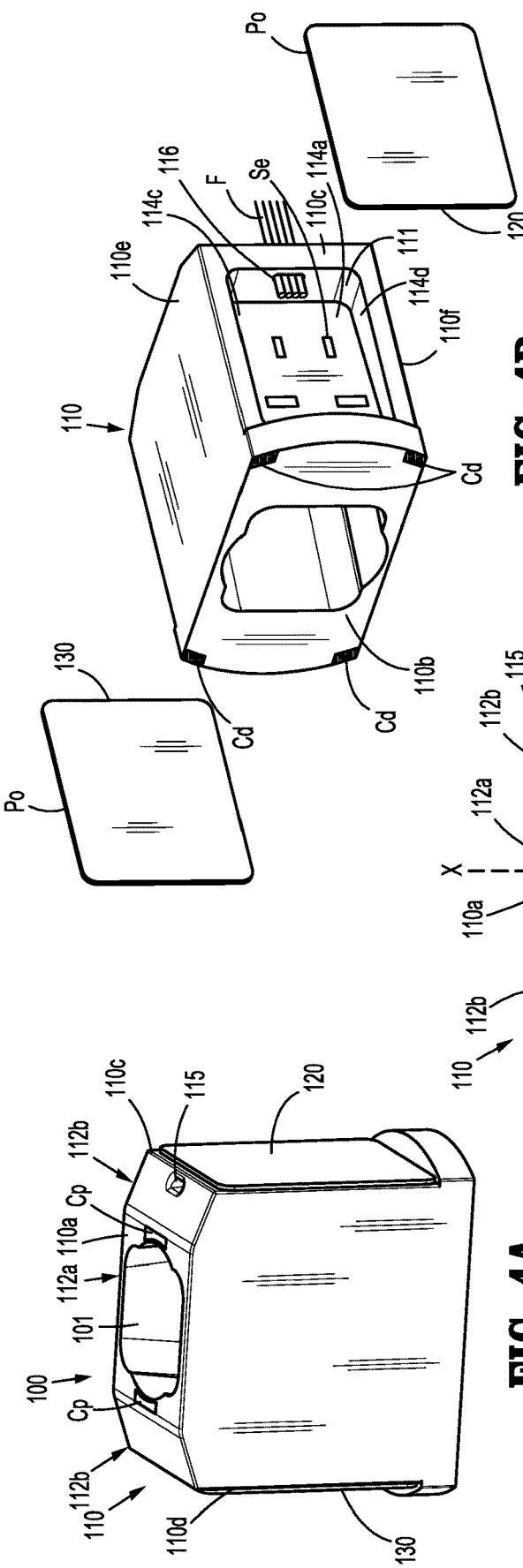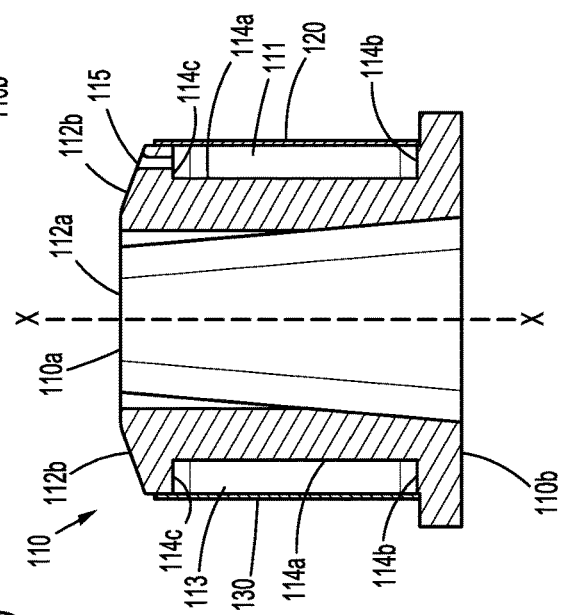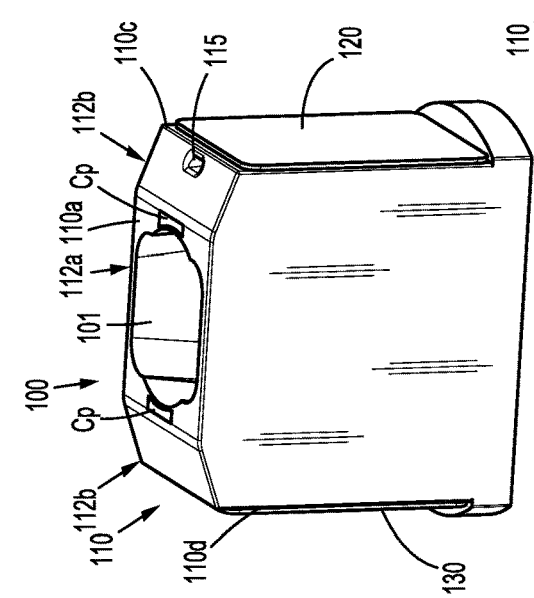

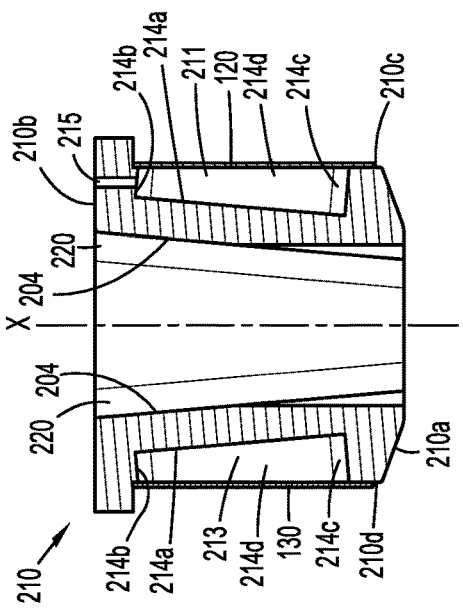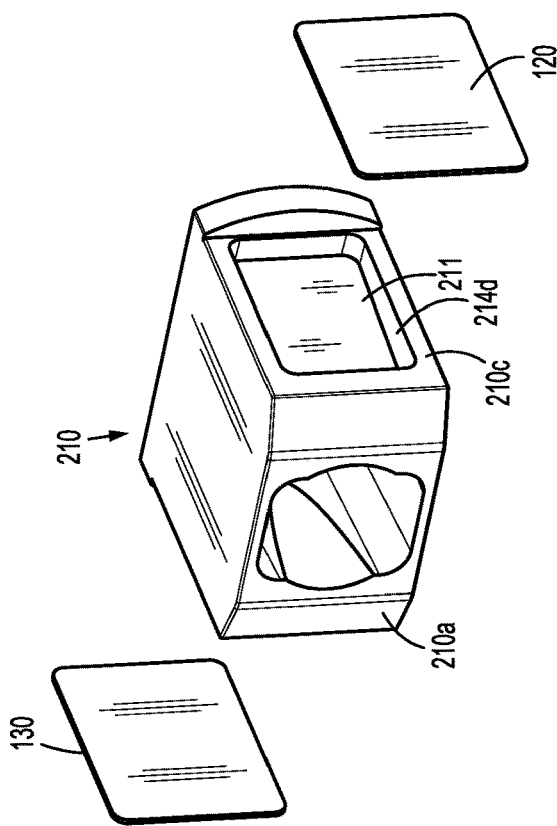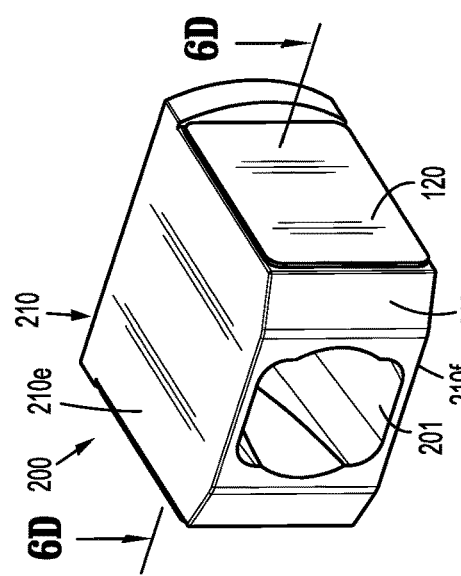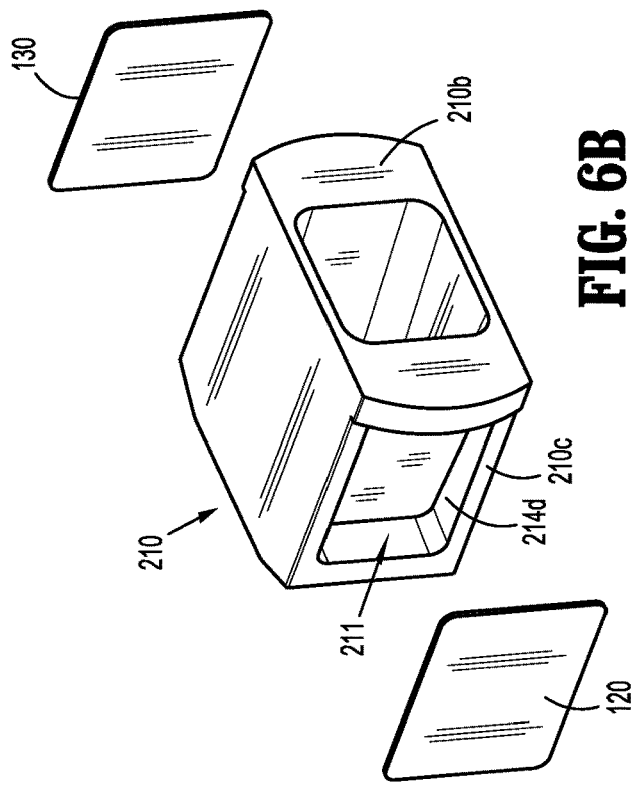

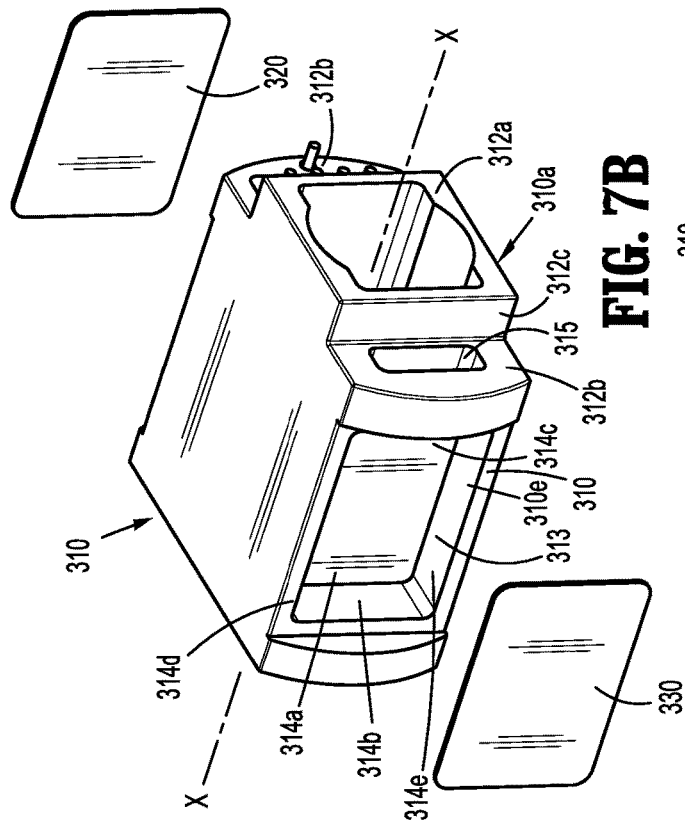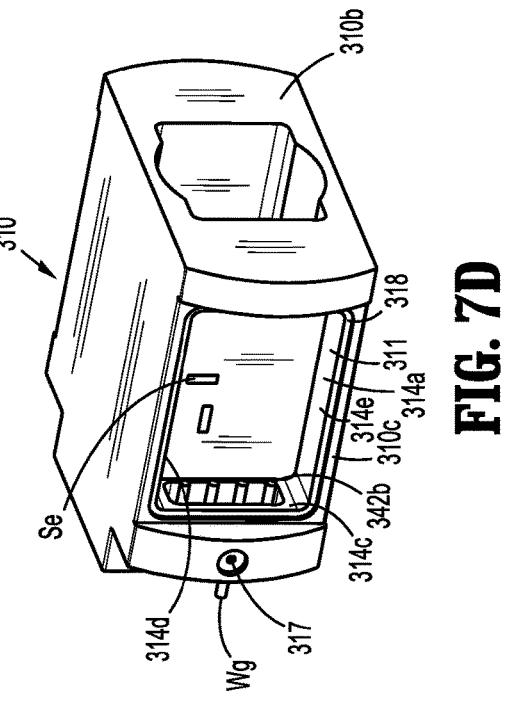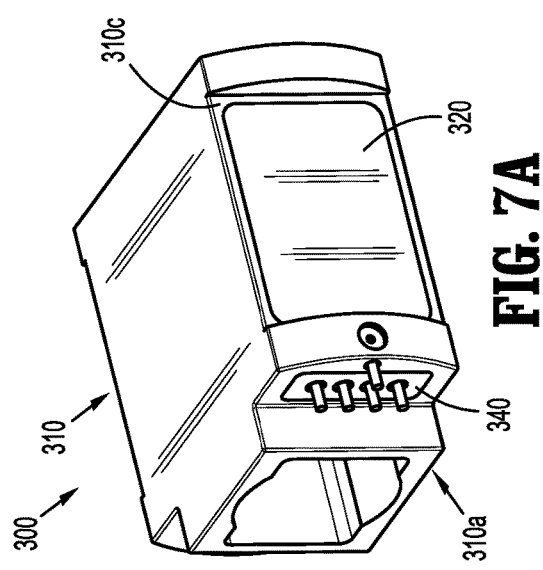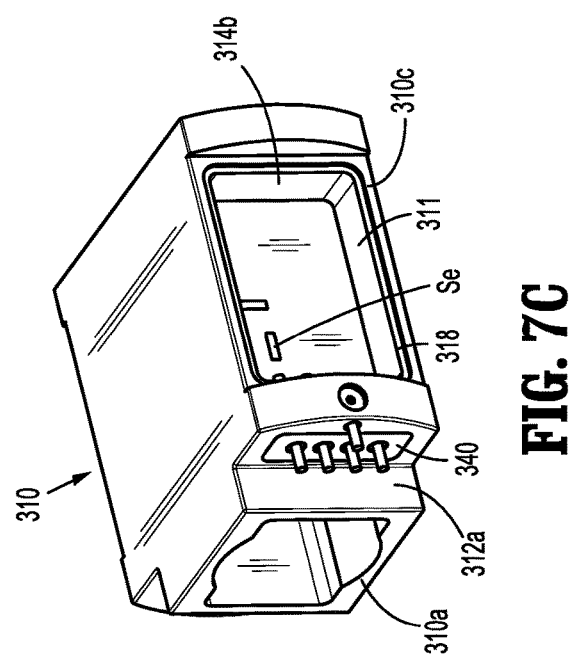

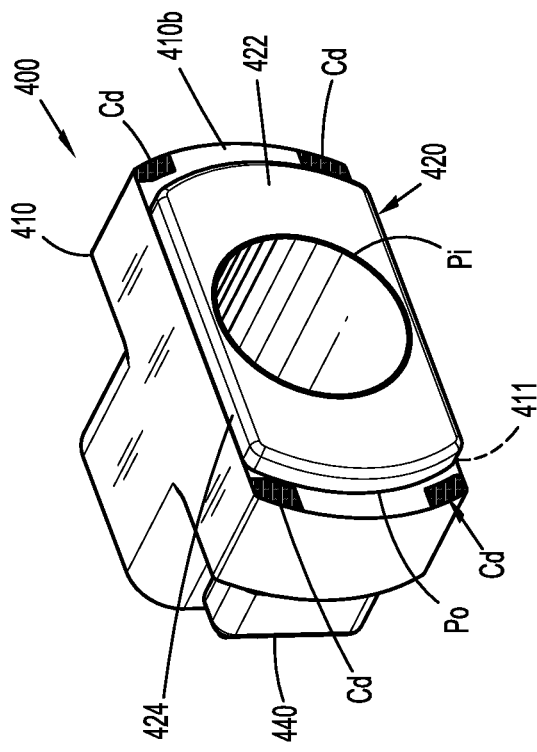
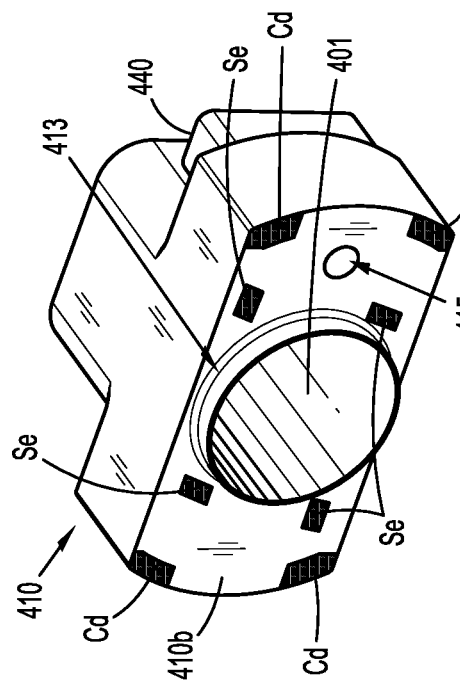
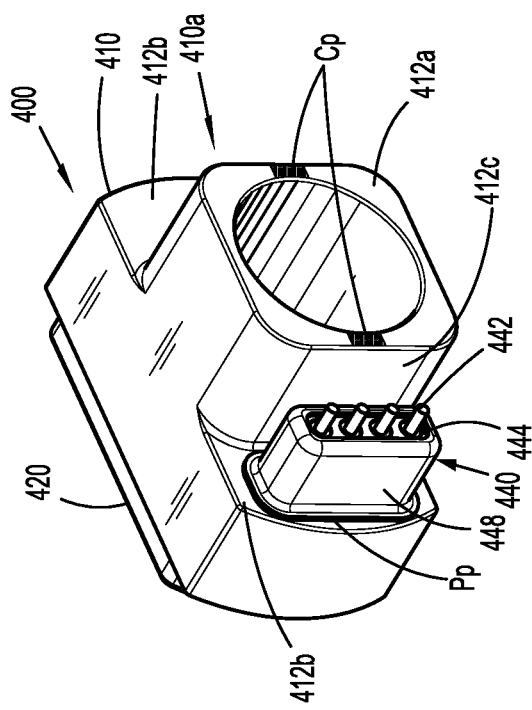
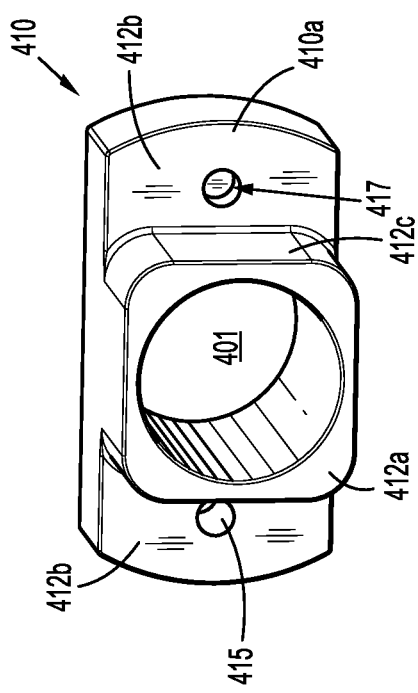
FIG. 10B
FIG. 10D
FIG. 10A
FIG. 10C

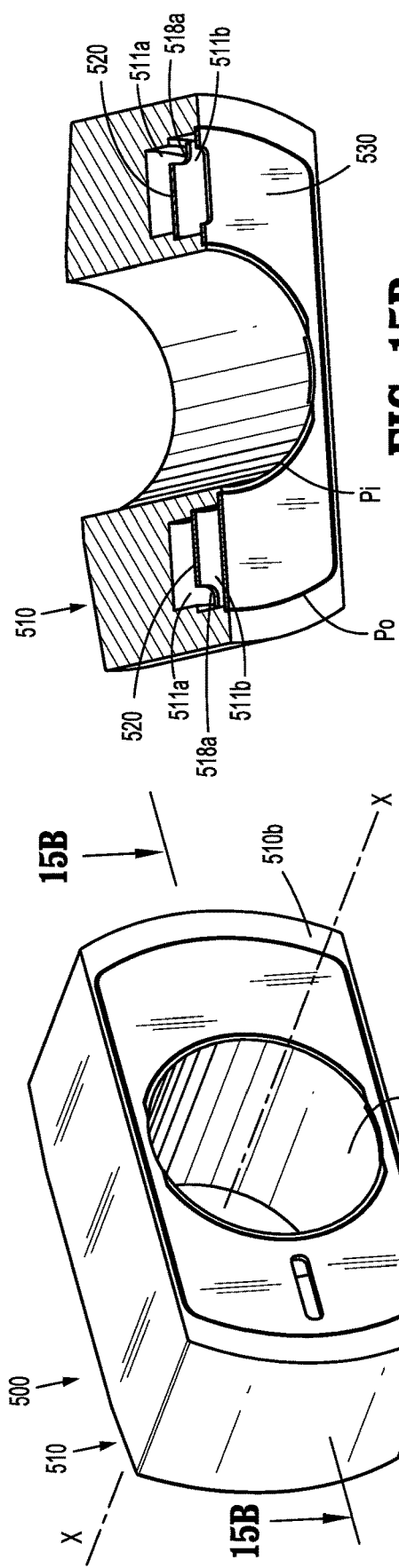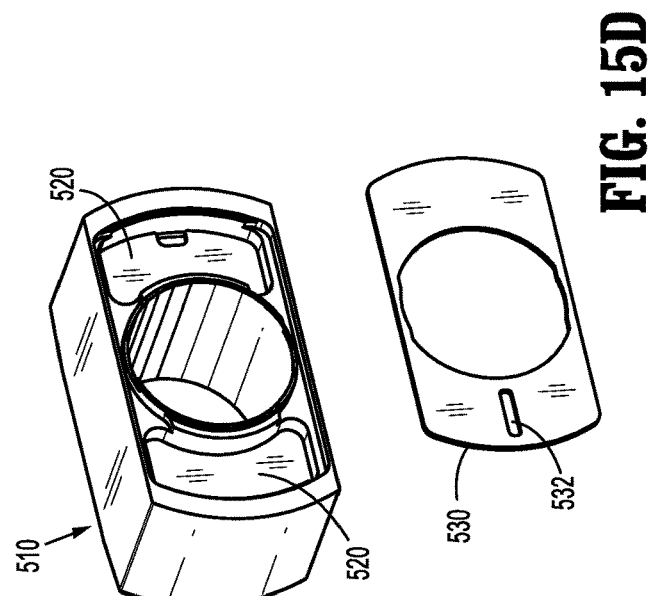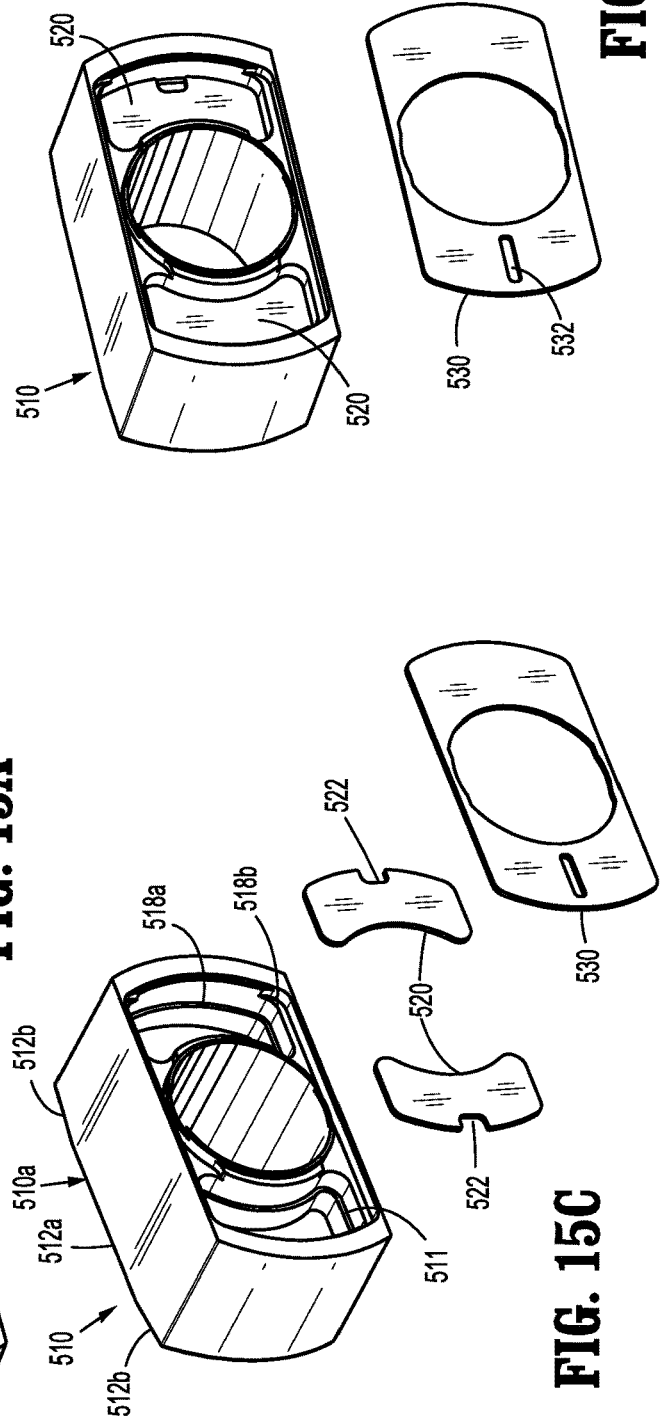

HERMETIC FORCE SENSORS FOR SURGICAL DEVICES

CROSS-REFERENCE TO RELATED APPLICATIONS

This application claims the benefit of and priority to U.S. Provisional Patent Application No. 62/375,043 filed Aug. 15, 2016, the entire disclosure of which is incorporated by reference herein.

TECHNICAL FIELD

The present disclosure relates generally to surgical devices. More particularly, the present disclosure relates to force sensors for powered surgical devices.

BACKGROUND

Force sensors (e.g., load reading sensors) are known, and have been used to enhance control of functions in a surgical device, such as a surgical stapling instrument. By using a load reading sensor, the clamping, stapling, and cutting forces of the surgical device can be monitored and used to facilitate these various functions. The load reading sensor can be used to detect pre-set loads and cause the surgical device to react to such a response. For example, during clamping of thick tissue, the load will rise to a pre-determined limit where the surgical device can slow clamping to maintain the clamping force as the tissue relaxes. This allows for clamping of thick tissue without damage to such tissue (e.g., serosa tears). One such example is the firing of a circular stapler type surgical device to create an anastomosis for a powered EEA device (e.g., End-to-End Anastomosis device). The intelligence of such a surgical device is at a higher product cost compared to currently available disposable units and thus would benefit if such intelligent devices are reusable.

Reusable surgical devices must be cleaned (e.g., disinfected) using high pH solutions and sterilized prior to subsequent uses. The most common method of sterilization is the use of autoclaving. Autoclaving utilizes high pressure superheated steam (e.g., 37 PSI @ 137° C. for 18 minutes). Such an environment is known to damage various electronic components and thus a need exists for sensors that can withstand high pH cleaning and sterilizations.

SUMMARY

The force sensors of the present disclosure are hermetically sealed and configured to withstand environmental stresses associated with cleaning and sterilization (e.g., autowashing and/or autoclaving), thereby rendering the force sensors more durable for re-use.

In one aspect of the present disclosure, a force sensor includes a substrate, a plurality of sensing elements, and a plate. The substrate includes a central aperture extending along a longitudinal axis of the substrate, and has a proximal surface, a distal surface, a first side surface, a second side surface, a top surface, and a bottom surface. A recess is defined within at least one of the distal surface, the first side surface, the second side surface, the top surface, or the bottom surface of the substrate. The plurality of sensing elements are disposed within the recess, and the plate is disposed over the recess and mounted to the substrate to hermetically seal the plurality of sensing elements within the substrate.

In embodiments, the recess is a first recess defined in the first side surface of the substrate. The first recess includes a back wall, a proximal-facing wall, a distal-facing wall, a top wall, and a bottom wall. In some embodiments, the back wall, the proximal-facing wall, the distal-facing wall, the top wall, and the bottom wall are all substantially planar. In some embodiments, the back wall is angled with respect to the longitudinal axis of the substrate, and the proximal-facing and distal-facing walls are angled with respect to the back wall. The substrate may include a second recess defined in the second side surface of the substrate.

The substrate may include a through hole extending through a wall of the recess and the proximal surface of the substrate. In embodiments, at least one wire is coupled to the plurality of sensing elements disposed within the recess and extends through the through hole. In some embodiments, a sealant is disposed within the through hole filling a space defined between an outer diameter of the wire and an inner diameter of the through hole.

The force sensor may include a pin block assembly mounted to the substrate and in communication with the through hole of the substrate. In embodiments, the pin block assembly includes a plurality of conductive pins, a plurality of glass seals, and a pin block housing including a plurality of openings. Each pin of the plurality of conductive pins extends through a glass seal of the plurality of glass seals which is disposed within an opening of the plurality of openings of the pin block housing. In some embodiments, the pin block housing is disposed within the through hole of the substrate. In certain embodiments, a distal portion of each pin of the plurality of pins is disposed within the recess of the substrate, and a proximal portion of each pin of the plurality of pins is disposed outside of the substrate.

In some embodiments, the pin block housing of the pin block assembly is disposed within a pin block cover, and the pin block cover is mounted to the substrate. In certain embodiments, a distal portion of each pin of the plurality of pins is disposed within the pin block cover, and a proximal portion of each pin of the plurality of pins extends proximally through the pin block cover.

The pin block assembly may be welded to the substrate. The plate may be welded to the first side surface of the substrate. The first side surface may include a recessed lip defined around an inner perimeter thereof, and the plate may be received within the recessed lip.

The substrate may include wall sections that define the central aperture, and the wall sections may be angled with respect to the longitudinal axis of the substrate.

In embodiments, the recess is a distal recess defined in the distal surface of the substrate. In embodiments, the recess is defined in at least two of the distal surface, the first side surface, the second side surface, the top surface, or the bottom surface of the substrate.

In embodiments, the force sensor is disposed between a connector housing and a trocar connector housing of an adapter assembly of a surgical device. The surgical device includes a powered handle assembly, the adapter assembly, and an end effector releasably secured to the connector housing of the adapter assembly. The force sensor is configured to measure forces exhibited by the end effector along a load path.

In another aspect of the present disclosure, a force sensor includes a substrate, a plurality of sensing elements, a plate, and a pin block assembly. The substrate includes a proximal surface, a distal surface, a first side surface, a second side surface, a top surface, and a bottom surface. A recess is defined within at least one of the distal surface, the first side surface, the second side surface, the top surface, or the bottom surface of the substrate, and a through hole extends through the substrate from the recess to the proximal surface. The plurality of sensing elements are disposed within the recess, and the plate is disposed over the recess and mounted to the substrate. The pin block assembly is mounted to the substrate and is in communication with the through hole of the substrate. The pin block assembly includes a plurality of conductive pins, a plurality of glass seals, and a pin block housing including a plurality of openings. Each pin of the plurality of conductive pins extends through a glass seal of the plurality of glass seals which is disposed within an opening of the plurality of openings of the pin block housing. The plate and the pin block assembly hermetically seal the plurality of sensing elements within the substrate. The pin block housing and/or the plate may be welded to the substrate.

The pin block housing may be disposed within the through hole of the substrate. In some embodiments, a distal portion of each pin of the plurality of pins is disposed within the recess of the substrate, and a proximal portion of each pin of the plurality of pins is disposed outside of the substrate.

The pin block housing of the pin block assembly may be disposed within a pin block cover. The pin block cover may be mounted to the substrate and in fluid communication with the through hole of the substrate. In some embodiments, the pin block cover is welded to the pin block housing around an entire inner perimeter of a proximal opening of the pin block cover. In some embodiments, a distal portion of each pin of the plurality of pins is disposed within the pin block cover, and a proximal portion of each pin of the plurality of pins extends proximally through the pin block cover.

In embodiments, the force sensor is disposed between a connector housing and a trocar connector housing of an adapter assembly of a surgical device. The surgical device includes a powered handle assembly, the adapter assembly, and an end effector releasably secured to the connector housing of the adapter assembly. The force sensor is configured to measure forces exhibited by the end effector along a load path.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein:

FIG. 3A is a perspective view of a distal end portion of the adapter assembly of FIGS. 1 and 2, with an outer sleeve of the adapter assembly removed therefrom;

FIG. 3B is an enlarged perspective view of a connector housing of the adapter assembly of FIG. 3A;

FIG. 3C is an enlarged perspective view of a trocar connection housing of the adapter assembly of FIG. 3A;

FIG. 4A is a perspective view of a force sensor of the surgical device of FIGS. 1-3A;

FIG. 4B is a perspective view, with parts separated, of the force sensor of FIG. 4A;

FIG. 4C is a cross-sectional view of the force sensor of FIGS. 4A and 4B;

FIG. 6A is a perspective view of a force sensor in accordance with yet another embodiment of the present disclosure;

FIGS. 6B and 6C are perspective views, with parts separated, of the force sensor of FIG. 6A;

FIG. 6D is a cross-sectional view the force sensor of FIGS. 6A-6C, as taken through 6D-6D of FIG. 6A;

FIG. 7A is a perspective view of a force sensor in accordance with another embodiment of the present disclosure;

FIG. 7B is a perspective view of the force sensor of FIG. 7A, illustrating a substrate thereof with first and second plates separated from the substrate;

FIGS. 7C and 7D are perspective views of the substrate of the force sensor of FIGS. 7A and 7B, including a pin block assembly;

FIGS. 10A and 10B are perspective views of a force sensor in accordance with another embodiment of the present disclosure;

FIGS. 10C and 10D are perspective views, respectively, of the force sensor of FIGS. 10A and 10B, illustrating a substrate thereof;

FIG. 15A is a perspective view of a force sensor in accordance with another embodiment of the present disclosure;

FIG. 15B is a cross-sectional perspective view of the force sensor of FIG. 15A, as taken through 15B-15B of FIG. 15A;

FIG. 15C is a perspective view, with parts separated, of the force sensor of FIGS. 15A and 15B;

FIG. 15D is a perspective view of the force sensor of FIGS. 15A-15C, with a distal plate separated from a substrate of the force sensor;

DETAILED DESCRIPTION

Figure 1:
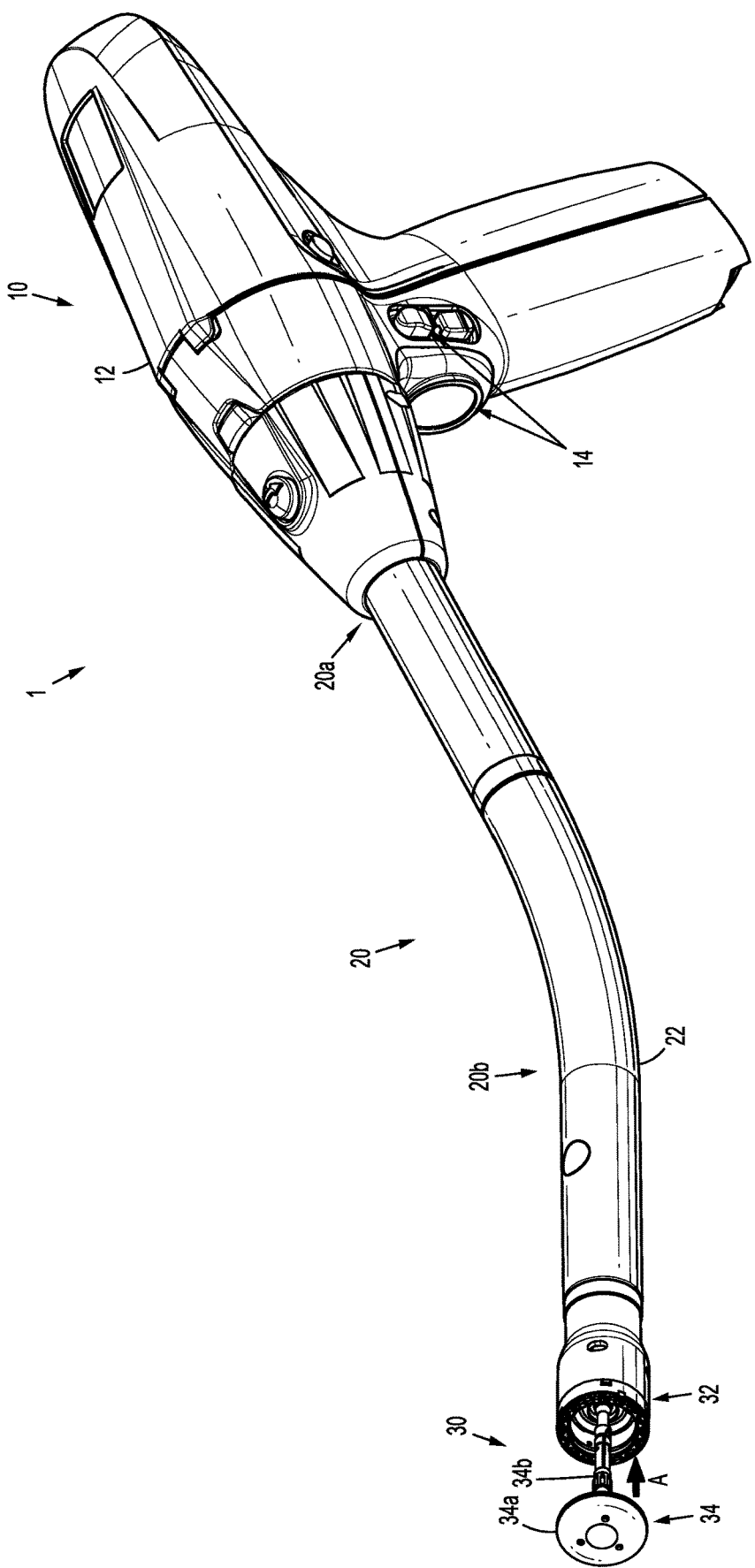
FIG. 1 is a perspective view of a surgical device in accordance with an embodiment of the present disclosure.

The force sensors of the present disclosure include hermetically sealed substrates that protect sensing elements of, e.g., surgical devices, from harsh environments, such as autowashing and/or autoclaving. The force sensors include a substrate including at least one recess defined therein for housing sensing elements, such as strain gauges and their supporting electronics, which are sealed from the outside environment by the use of one or more plates, sealants, and/or pin block assemblies to create a protective leak-proof barrier to the sensing elements.

Embodiments of the present disclosure are now described in detail with reference to the drawings in which like reference numerals designate identical or corresponding elements in each of the several views. Throughout this description, the term "proximal" refers to a portion of a device, or component thereof, that is closer to a hand of a user, and the term "distal" refers to a portion of the device, or component thereof, that is farther from the hand of the user. Directional reference terms, such as "top," "bottom," "back," "side," and the like, are intended to ease description of the embodiments and are not intended to have any limiting effect on the ultimate orientations of the surgical devices, or any parts thereof.

Turning now to FIG. 1, a surgical device 1, in accordance with an embodiment of the present disclosure, is in the form of a powered handheld electromechanical instrument, and includes a powered handle assembly 10, an adapter assembly 20, and a tool assembly or end effector 30 including a loading unit 32 having a plurality of staples (not shown) disposed therein and an anvil assembly 34 including an anvil head 34a and an anvil rod 34b. The powered handle assembly 10 is configured for selective connection with the adapter assembly 20 and, in turn, the adapter assembly 20 is configured for selective connection with the end effector 30.

While described and shown as including adapter assembly 20 and end effector 30, it should be understood that a variety of different adapter assemblies and end effectors may be utilized in the surgical device of the present disclosure. For a detailed description of the structure and function of exemplary surgical devices, reference may be made to commonly owned U.S. patent application. Ser. No. 14/991,157 ("the '157 application"), filed on Jan. 8, 2016, and Ser. No. 15/096,399 ("the '399 application"), filed on Apr. 12, 2016, the entire contents of each of which are incorporated herein by reference.

With continued reference to FIG. 1, the handle assembly 10 includes a handle housing 12 housing a power-pack (not shown) configured to power and control various operations of the surgical device 1, and a plurality of actuators 14 (e.g., finger-actuated control buttons, knobs, toggles, slides, interfaces, and the like) for activating various functions of the surgical device 1. For a detailed description of an exemplary handle assembly, reference may be made to the '399 application, the entire contents of which was previously incorporated herein by reference.

Figure 2:
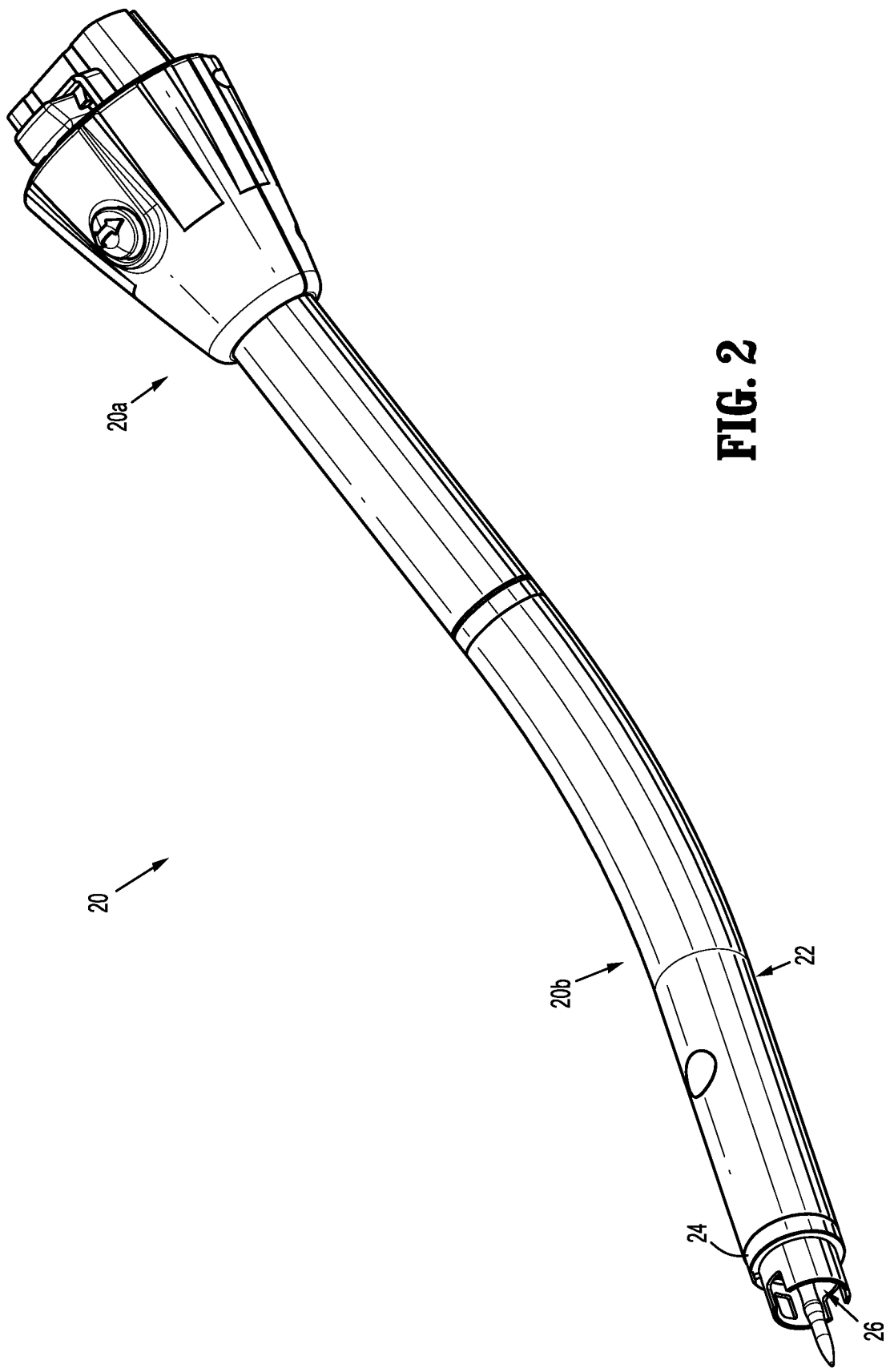
FIG. 2 is a perspective view of an adapter assembly of the surgical device of FIG. 1.

Referring now to FIG. 2, in conjunction with FIG. 1, the adapter assembly 20 includes a proximal portion 20a configured for operable connection to the handle assembly 10 (FIG. 1) and a distal portion 20b configured for operable connection to the end effector 30 (FIG. 1). The adapter assembly 20 includes an outer sleeve 22, and a connector housing 24 secured to a distal end of the outer sleeve 22. The connector housing 24 is configured to releasably secure an end effector, e.g., the end effector 30 (FIG. 1), to the adapter assembly 20.

The adapter assembly 20 will only further be described to the extent necessary to fully disclose the aspects of the present disclosure. For detailed description of an exemplary adapter assembly, reference may be made to the '157 application, the entire contents of which was previously incorporated herein by reference.

With reference now to FIG. 3A, in conjunction with FIG. 2, the adapter assembly 20 further includes a trocar assembly 26 that extends through a central aperture 101 (see e.g., FIG. 4A) of a force sensor 100 and a central aperture 29 (FIG. 3C) of a trocar connection housing 28. The trocar connection housing 28 releasably secures the trocar assembly 26 relative to the outer sleeve 22 (FIG. 2) of the adapter assembly 20. For a detailed description of an exemplary trocar connection housing, reference may be made to U.S. patent application Ser. No. 14/865,602 ("the '602 application"), filed on Sep. 25, 2015, the entire contents of which are incorporated herein by reference.

The force sensor 100 is disposed between the trocar connection housing 28 and the connector housing 24 of the adapter assembly 20, and is configured to measure forces along a load path. As shown in FIGS. 3C and 4A, the trocar connection housing 28 includes a distal surface 28a which interfaces with, and loads a proximal surface 110a of a body or substrate 110 of the force sensor 100 at proximal load contact areas "Cp". As shown in FIGS. 3B and 4B, a proximal surface 24a of the connector housing 24 defines a contact surface which loads a distal surface 110b of the substrate 110 of the force sensor 100 at distal load contact areas "Cd." Thus, for example, as the anvil assembly 34 (FIG. 1) is approximated towards the loading unit 32 of the end effector 30 during clamping and/or stapling of tissue, the anvil head 34a applies uniform pressure in the direction of arrow "A" (FIG. 1) against the distal end 24b of the connector housing 24 which, in turn, is transmitted to the distal load contact areas "Cd" of the force sensor 100.

Referring now to FIGS. 4A-4C, the force sensor 100 includes a substrate 110, and first and second plates 120, 130 bonded to the substrate 110 in a fluid tight manner. A central aperture 101 is defined through the substrate 110 and extends along a central longitudinal axis "X" of the substrate 110. The substrate 110 includes a proximal surface 110a and a distal surface 110b which are load bearing surfaces, as described above, that allow the substrate 110 to compress when loaded by the surgical device 1 (FIG. 1). The proximal surface 110a of the substrate 110 includes a central region 112a and lateral regions 112b extending laterally from the central region 112a. The central region 112a is substantially planar and extends along a plane lying substantially perpendicular to the central longitudinal axis "X" of the substrate 110. The lateral regions 112b are substantially planar and extend along planes disposed at angles with respect to the central region 112a that slope distally from the central region 112a to first and second side surfaces 110c, 110d of the substrate 110.

The first and second side surfaces 110c, 110d and top and bottom surfaces 110e, 110f extend between the proximal and distal surfaces 110a, 110b of the substrate 110. The first and second side surfaces 110c, 110d each define a recess 111, 113, respectively, therein for bonding of sensing elements "Se" (FIG. 4B), for example, strain gauges, therein. The first and second side surfaces 110c, 110d are substantially a mirror image of each other and allows for uniform strain along the force sensor 100. It should be understood, however, that the substrate 110 may be formed to include only one recess in either the first or second side surfaces 110c, 110d while maintaining a flex-type configuration (such as that of a simply supported beam) that allows for large strain upon deformation which, in turn, creates more signal and resists transient thermos or thermal variation shifts. The force sensor 100 self-aligns regardless of tolerance variation and upon loading, is forced against proximal load contact areas "Cp" and will flex, having constant flexure along its length.

The first and second recesses 111, 113 are each defined by a back wall 114a, a proximal-facing wall 114b, a distal-facing wall 114c disposed in spaced, opposed relation to the proximal-facing wall 114b, a top wall 114c, and a bottom wall 114d disposed in spaced, opposed relation to the top wall 114c. The back wall 114a extends along a plane that is substantially parallel to the central longitudinal axis "X" of the substrate 110. The proximal-facing wall 114b, the distal-facing wall 114c, the top wall 114c, and the bottom wall 114d extend outwardly from the back wall 114a and are oriented at about 90° relative to the back wall 114a. A through hole 115 extends through the distal-facing wall 114c of the first and/or second recesses 111, 113 and the respective lateral region 112b of the proximal surface 110a of the substrate 110. The angle of the lateral region 112b of the proximal surface 110a provides a strain relief on wires (see e.g., flex cable "F" in FIG. 4B) passed therethrough.

As shown in FIG. 4B, sensing elements "Se", e.g., strain gauges, are disposed within the first recess 111, along with associated components thereof (not shown), e.g., media layers, films, protective coatings, circuitry including electronic components, such as resistors, and conductive wires and/or traces, electronic and/or solder connectors, etc. The sensing elements "Se" are mounted in specific locations within the first recess 111 and in embodiments, to the back wall 114a of the first recess 111, and are connected together with a series of wires (not shown) to form a resistance bridge, e.g., a Wheatstone bridge, that can read a linear strain response of the substrate 110 when compressed, as is within the purview of those skilled in the art. In embodiments, the linear strain response is read using a single conditioner which may include an operational amplifier to enhance the signal.

A flex cable "F," which is coupled to the sensing elements "Se," exits the first recess 111 through the through hole 115 for electrical connection with electronics of the surgical device 1 (FIG. 1). For example, the flex cable "F" (FIG. 4B) extends through the through hole 115 of the substrate 110 for electrical connection with wires "W" (FIG. 3A) coupled to the trocar connection housing 28 which, in turn, are electrically connected to electronics (not shown) of the surgical device 1 (FIG. 1) for supplying power and reading force responses from the force sensor 100. Thus, when surgical device 1 (FIG. 1) is used in such a way to cause compression on the force sensor 100, the surgical device 1 can be programmed to perform a function with respect to the measured force.

A sealant 116 is disposed within the through hole 115 in a fluid tight manner with the flex cable "F" to maintain a hermetic seal within the first recess 111. The sealant 116 may be, for example, epoxies, RTV sealants, urethanes, acrylics, among other materials and/or encapsulates that can withstand sterilization, disinfection, and/or cleaning procedures to which the adapter assembly 20 (FIG. 1) may be subjected, as is within the purview of those skilled in the art.

The first and second plates 120, 130 are dimensioned to cover and seal the first and second recesses 111, 113, respectively. The first and second plates 120, 130 are mounted on the first and second side surfaces 110c, 110d, respectively, and secured thereto in a fluid tight manner. In embodiments, the first and second plates 120, 130 are welded to the first and second side surfaces 110c, 110d, respectively, by, for example, laser or electronic beam welding, around the entirety of an outer perimeter "Po" of the first and second plates 120, 130 to form a hermetic seal and leak-proof barrier to protect the sensing elements "Se" and associated components from the external environment (e.g., during cleaning and/or sterilization processes). The first and second plates 120, 130 may be fabricated from a metal, such as stainless steel (e.g., 304L/17-4 stainless steel), among other materials capable of achieving a desired yield as within the purview of those skilled in the art. The first and second plates 120, 130 have a minimal thickness so as to bend and to allow for a responsive signal from the substrate 110 upon loading.

In embodiments, the through hole 115 may be a series of through holes through which individual wires and/or cables may pass. In some embodiments, individual pins may be sealed within the series of through holes, for example, with sealants disposed within each through hole as described above, glass seals disposed within each through hole as described below, and/or o-rings placed on the pins within the each through hole.

While only the first recess 111 is shown having sensing elements "Se" mounted therein, and having a through hole 115 in communication therewith, it should be understood that, depending on the desired sensor configuration, the sensing elements "Se" may be mounted in either or both of the first or second recesses 111, 113, and either or both of the first or second recesses 111, 113 may include a through hole 115 therethrough. In embodiments, both the first and second recesses may include sensing elements, through holes, and first and second plates mounted thereto. In embodiments, the sensing elements may be disposed in only one of the first or second recesses and a through hole may be defined in only the recess including the sensing elements. In some embodiments in which only one of the first or second recesses includes sensing elements, only the respective first or second plate may be secured to the first or second side surface containing the sensing elements. In certain embodiments, both the first and second plates may be secured to the substrate where a wire trace is utilized for electrical communication between the first and second recesses.

Figure 5B:
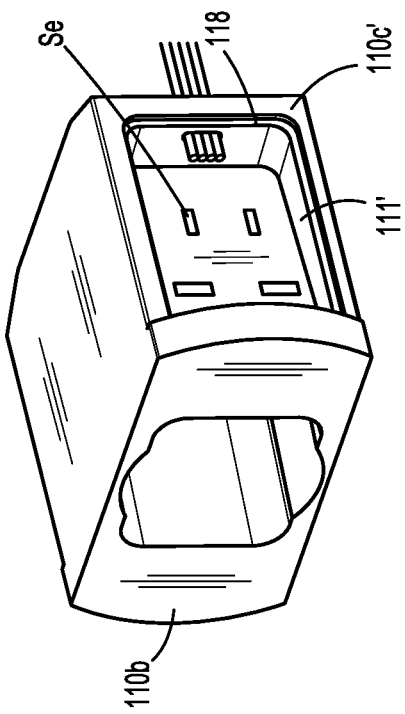
FIG. 5B is a perspective view of the force sensor of FIG. 5A, illustrating a substrate thereof.
Figure 5A:
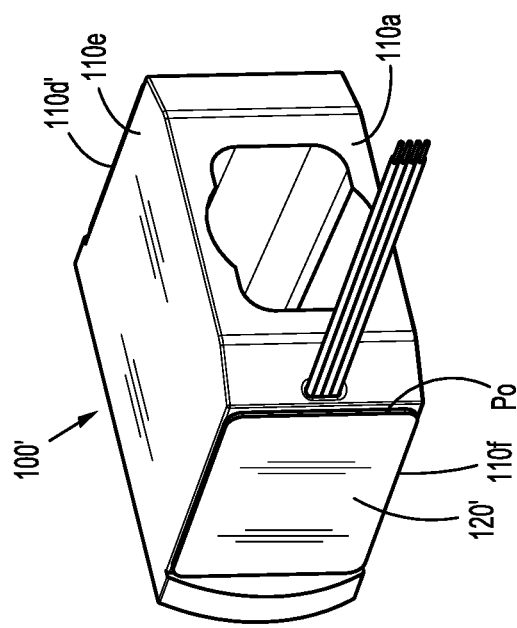
FIG. 5A is a perspective view of a force sensor in accordance with another embodiment of the present disclosure.

Referring now to FIGS. 5A and 5B, a force sensor 100' is shown in accordance with another embodiment of the present disclosure. The force sensor 100' is substantially the same as the force sensor 100, and therefore will only be described herein with respect to the differences therebetween. The force sensor 100' includes a substrate 110', a first plate 120', and a second plate (not shown). The substrate 110' includes a proximal surface 110a, a distal surface 110b, a first side surface 110c' defining a first recess 111' therein, a second side surface 110d' defining a second recess (not shown) therein, and top and bottom surfaces 110e, 110f. While the first side surface 110c' is described singularly herein, it should be understood that the second side surface 110d' may be substantially similar to the first side surface 110c', or the structure may vary depending on the desired sensor configuration as described above with regard to substrate 110.

The first side surface 110c' includes a recessed lip 118 extending around an inner perimeter thereof. The recessed lip 118 is configured to receive the first plate 120' such that the first plate 120' is disposed in spaced relation relative to the sensing elements "Se" disposed within the first recess 111' and is flush with, and sealed to, the first side surface 110c' of the substrate 110', for example, by welding the first plate 120' around an entire outer perimeter "Po" of the first plate 120'.

Referring now to FIG. 6A-6D, a force sensor 200 is shown in accordance with another embodiment of the present disclosure. The force sensor 200 is substantially similar to the force sensor 100 and therefore, will only be described herein with respect to the differences therebetween. The force sensor 200 includes a substrate 210 having a central aperture 201 defined therethrough. The substrate 210 includes a proximal surface 210a, a distal surface 210b, a first side surface 210c defining a first recess 211 therein, a second side surface 210d defining a second recess 213 therein, and top and bottom surfaces 210e, 210f. First and second plates 120, 130 are configured to be mounted and sealed to the first and second side surfaces 210c, 210d, respectively, to hermetically seal the first and second recesses 211, 213. It should be understood that while the first and second plates 120, 130 are shown mounted to the first and second side surfaces 210c, 210d of the substrate 210, the first and second side surfaces 210c, 210d may each include a recessed lip configured to receive the first and second plates 120, 130 therein, as described above with regard to substrate 110'.

As specifically shown in FIG. 6D, the central aperture 201 of force sensor 200 includes relief features 220 to maintain angled wall sections 204 that define the central apertures 201. The first and second recesses 211, 213 are each defined by a back wall 214a, a proximal-facing wall 214b, a distal-facing wall 214c disposed in spaced, opposed relation to the proximal-facing wall 214b, a top wall 214c, and a bottom wall 214d disposed in spaced, opposed relation to the top wall 214c. The back wall 214a extends along a plane that is angled with respect to a central longitudinal axis "X" of the substrate 210, such that the respective first or second recess 211, 213 tapers distally. The proximal-facing wall 214b, the distal-facing wall 214c, the top wall 214c, and the bottom wall 214d extend outwardly from the back wall 214a. The proximal-facing wall 214b and the distal-facing wall 214c taper laterally towards the respective first or second side surface 210c, 210d, and the top wall 214c and the bottom wall 214 are substantially perpendicular to the back wall 214a. A through hole 215 extends through the proximal-facing wall 214b of the first recess 211 and the distal surface 110b of the substrate 110.

The angled wall sections 204 of the central aperture 201, as well as the angled walls (e.g., the back wall 214a, the proximal-facing wall 214b, and the distal-facing wall 214c) of the first and second recesses 211, 213 eliminates or reduces pure compression during loading of the force sensor 200, allowing the substrate 210 to be subjected to both compression and bending. The configuration of the first and second recesses 211, 213 allows for increased strain (e.g., substrate deflection) which can produce a larger strain range which, in turn, allows for more signal response from the force sensor 200 to improve accuracy.

As described above with respect to substrate 110, sensing elements (not shown) are disposed within the first and/or second recess 211, 213, along with and associated components thereof (not shown), a flex cable (not shown) exits the first and/or second recess 211, 213 via the through hole 215 of the substrate 210, and a sealant (not shown) is disposed within the through hole 215 in a fluid tight manner with the flex cable to maintain a hermetic seal within the first and/or second recess 211, 213. It should be understood the structure of the first and/or second recesses 211, 213, as well as the through hole 215 may vary, as described above with regard to substrate 110, depending on the desired sensor configuration.

Referring now to FIGS. 7A-7E, a force sensor 300 is shown in accordance with another embodiment of the present disclosure. The force sensor 300 includes a substrate 310, first and second plates 320, 330, and a pin block assembly 340. The substrate 310 is substantially similar to the substrates 110, 110' described above and therefore, will only be described herein with respect to the differences therebetween. The substrate 310 includes a proximal surface 310a and a distal surface 310b, which are load bearing surfaces as described above, a first side surface 310c including a first recess 311 defined therein, and a second side surface 310d including a second recess 313 defined therein. Sensing elements "Se" are mounted inside the first and/or second recesses 311, 313 of the substrate 310, as described above, for example, with regard to substrate 110, and the first and second plates 320, 330 are mounted over the first and second recesses 311, 313, respectively, and sealed to the respective first and second side surfaces 310c, 310d (e.g., by welding).

While each of the first and second recesses 311, 313 are shown having a back wall 314a, a proximal-facing wall 314b, a distal-facing wall 314c, a top wall 314d, and a bottom wall 314e that are all planar, it should be understood that the first and second recesses 311, 313 may include angled walls as described above with respect to first and second recesses 211, 213 of substrate 200 of force sensor 200. Additionally, while the first and second plates 310, 320 are shown as being received within recessed lips 318 of the respective first and second side surfaces 310c, 310d, it should be understood that the first and second plates 320, 330 may overly the first and second side surfaces 310c, 310d as described above, for example, with respect to force sensor 100.

As specifically shown in FIG. 7B, the proximal surface 310a of the substrate 310 is a stepped surface including a central region 312a, lateral regions 312b, and intermediate regions 312c interconnecting the central and lateral regions 312a, 312b. The central region 312a is substantially planar and extends along a plane lying substantially perpendicular to the central longitudinal axis "X" of the substrate 310, and the lateral regions 312b are also planar and extend along a plane lying substantially perpendicular to the central longitudinal axis "X" of the substrate 310 in longitudinally spaced and distal relation to the central region 312a. The intermediate regions 312c are substantially planar and extend along a plane lying substantially parallel to the central longitudinal axis "X" of the substrate 310. It should be understood that the proximal surface 310a may also be configured to include angled lateral walls as described, for example, with respect to proximal surface 110a of substrate 110 of force sensor 100, and conversely, the proximal surfaces 110a, 210a of the substrates 110, 110', 210 may alternatively include the stepped configuration of proximal surface 310a of substrate 310.

A through hole 315 is defined in the substrate 310 that extends through the distal-facing wall 314c of the first and/or second recess 311, 313 and a respective lateral region 312b of the proximal surface 310a of the substrate 310 such that the first and/or second recess 311, 313 is in communication with the exterior of the substrate 310. In some embodiments, a pass through 317 (see e.g., FIG. 7D) may be provided in the substrate 310 adjacent the through hole 315 for passage of a ground wire "Wg."

Figure 8B:
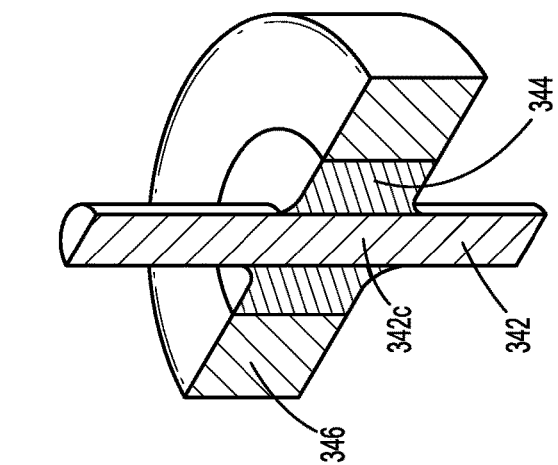
FIG. 8B is a schematic, cross-sectional illustration of a glass-to-metal pin transition in the pin block assembly of FIG. 8A.
Figure 8A:
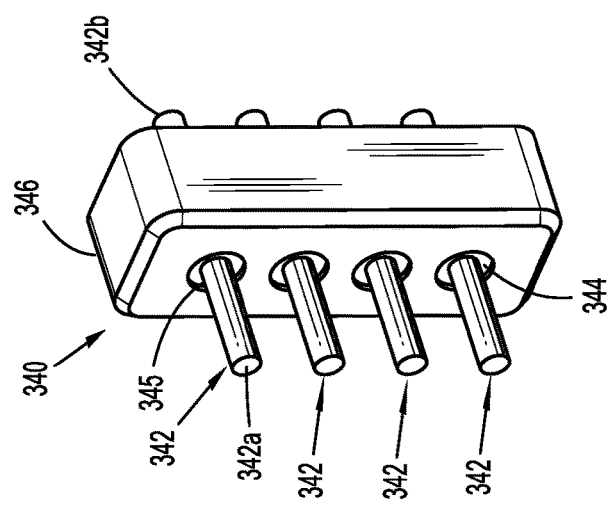
FIG. 8A is a perspective view of a pin block assembly of the force sensor of FIGS. 7A-7E.
Figure 7E:
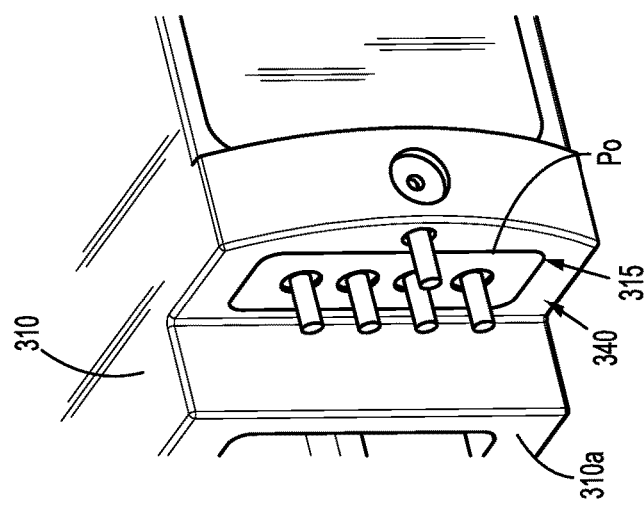
FIG. 7E is an enlarged perspective view of a proximal portion of the force sensor of FIGS. 7A-7D.

As best seen in FIGS. 7C-7E, the pin block assembly 340 is disposed and fixedly secured within the through hole 315 of the first recess 311 of the substrate 310. However, it should be understood that either or both the first or second recess 311, 313 may include a pin block assembly 340. As shown in FIGS. 8A and 8B, the pin block assembly 340 includes a plurality of conductive pins 342, with each pin 342 extending through a glass substrate or seal 344 disposed within an opening 345 of a pin block housing 346. The plurality of conductive pins 342 are formed from metals, such as copper, iron, nickel and alloys thereof. In embodiments, the plurality of conductive pins 342 are formed from low thermal expansion alloys, such as Alloy 52 (NILO®, which is a registered trademark owned by Inco Alloys International, Inc.). Each conductive pin 342 includes a proximal portion 342a, a distal portion 342b, and a central portion 342c disposed therebetween. The central portion 342c is disposed within the glass substrate 344 and the proximal and distal portions 342a, 342b extend proximally and distally, respectively, therefrom.

The pin block housing 346 includes a plurality of openings 345 defined therethrough that correspond to the desired number of conductive pins 342. The conductive pins 342 are sealed with the pin block housing 346 by the glass substrates 344. The glass substrates 344 are formed from glass, silicates, ceramics, and composites thereof that are capable of withstanding large temperature variations associated with, for example, autoclaving and/or autowashing procedures, and, in some embodiments, the glass substrates have an internal porosity which provides flexibility to the glass substrate to minimize or prevent fracture and/or breakage thereby strengthening the seal. In embodiments, the glass substrates 344 are formed from a polycrystalline ceramic, such as KRYOFLEX®, which is a registered trademark owned by Pacific Aerospace and Electronics, Inc.

In a method of forming the pin block assembly 340, the pin block housing 346 is placed in a fixture and each conductive pin 342 is positioned through, and centered within, an opening 345 of the pin block housing 346. Glass is heated to its melting point and poured into each opening 345 so that the glass flows into and fills the space between the inner diameter of the opening 345 of the pin block housing 346 and the outer diameter of the conductive pin 342. Upon cooling, the glass solidifies and seals the conductive pins 342 to the pin block housing 346. In embodiments, solid glass particles are pre-assembled and heated to allow the glass to flow and make the seal.

Depending on the choice of materials, in another method of forming the pin block assembly 340, the pin block housing 346 may also be heated such that the inner diameter of the openings 345 expands upon heating and then shrinks upon cooling to form a compression seal thereby enhancing the seal of the pin block assembly 340. For example, materials for various components of a pin block assembly may be selected based on, among other things, their coefficient of thermal expansion. In embodiments, the pin block housing 346 is formed from 17-4 PH stainless steel and the conductive pins 342 are formed from NILO®, a nickel-iron alloy which has minimal to no thermal expansion. When heated, the openings 345 of the pin block housing 346 that will contain the glass seals 344 expand. After the glass is melted and the pin block assembly 340 is cooled, the openings 345 shrink and compress the conductive pins 342 (that did not expand or that minimally expanded upon heating), thereby forming a compression seal.

Referring again to FIG. 7E, the pin block housing 346 is positioned within the through hole 315 of the substrate 310 and is secured therein in a fluid tight manner. In embodiments, the pin block housing 346 is welded along its entire outer perimeter "Po" to the substrate 310 to form a fully hermetic assembly of the pin block assembly 340 to the substrate 310. As the conductive pins 342 are sealed within the pin block housing 346 via the glass substrates 344 and the pin block housing 346 is welded to the substrate 310, the entire force sensor 300 is hermetically sealed without the use of sealants. It should be understood that, for example, the substrates 110, 110', 220 may include a pin block assembly through the through hole(s) of the substrates 110, 110', 220 as an alternative to the use of the sealants 116. The integrity of glass seals is not sacrificed over time by chemical attack and/or degradation which may occur with sealants. Sealants may break down over time and, if not processed properly and/or applied correctly, may leak. Glass seals, on the other hand, are highly reliable and consistent once the process and components are dialed in.

As shown, for example, in FIGS. 7C and 7D, the proximal portions 342a of the plurality of conductive pins 342 are disposed external of the substrate 310 and the distal portions 342b of the plurality of conductive pins 342 are within the first recess 311 of the substrate 310. Wires (not shown) are connected (e.g., soldered) to the sensing elements "Se" which are disposed within the first recess 311 of the substrate 310 in a bridge configuration (e.g., a Wheatstone bridge), and soldered to the distal portions 342b of the plurality of conductive pins 342 so that electrical signals may exit the substrate 310 in order to supply power and read force responses from the force sensor 300.

Figure 9:
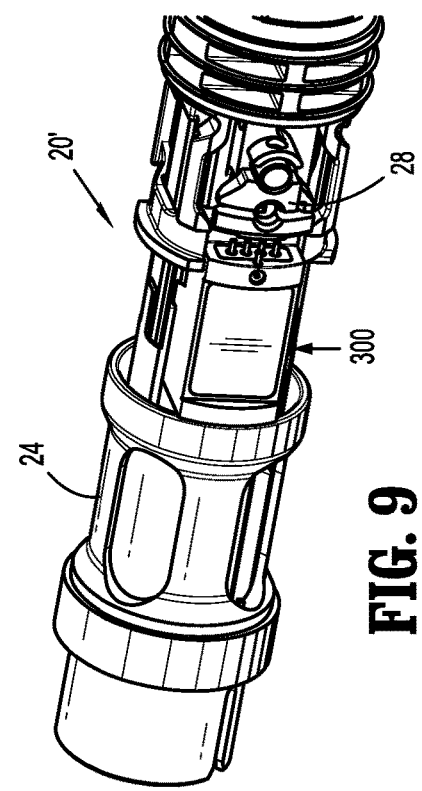
FIG. 9 is a perspective view of a distal end portion of an adapter assembly of a surgical device including the force sensor of FIGS. 7A-7E, with an outer sleeve of the adapter assembly removed therefrom.

As shown in FIG. 9, the force sensor 300 is disposed between a trocar connection housing 28 and a connector housing 24 of an adapter assembly 20' of a surgical device 1 (FIG. 1) in a similar manner as force sensors 100, 100', 200 to measure forces along a load path and enhance control of a function of the surgical device 1, as described in further detail below.

Referring now to FIGS. 10A-10E, another embodiment of a force sensor 400 is shown. The force sensor 400 includes a substrate 410, a first or distal plate 420, and a pin block assembly 440. The substrate 410 includes a central aperture 401 defined therethrough and extending between a proximal surface 410a and a distal surface 410b. The proximal surface 410a interfaces with a trocar connection housing 28 (see e.g., FIG. 1), and the distal surface 410b interfaces with a connector housing 24 (see e.g., FIG. 1). The proximal and distal surfaces 410a, 410b are load bearing surfaces that allow the substrate 410 to flex when loaded by a surgical device 1 (FIG. 1), and include proximal and distal load contact areas "Cp" and "Cd," respectively, as described above, for example, with respect to force sensor 100.

The proximal surface 410a of the substrate 410 is a stepped surface that is substantially similar to the proximal surface 310a of substrate 310, described above, and includes a central region 412a which is an outwardly protruding loading portion, lateral regions 412b, and intermediate regions 412c interconnecting the central and lateral regions 412a, 412b. The distal surface 410b is a substantially planar surface including a distally extending flange 413 extending around the central aperture 401 of the substrate 410.

Figure 10E:
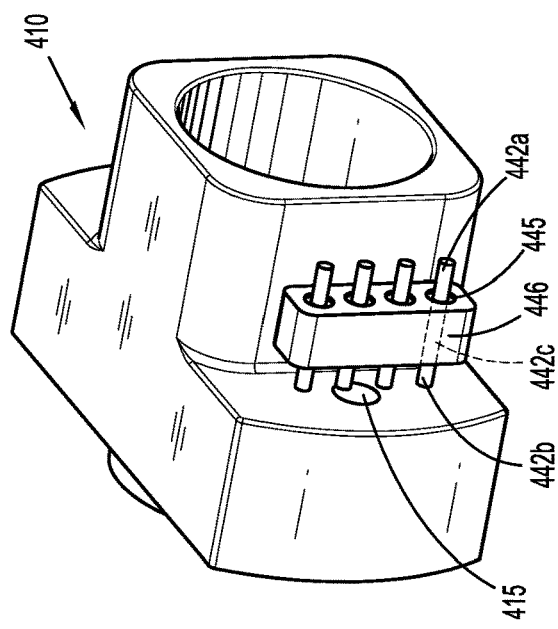
FIG. 10E is a side perspective view of the substrate of the force sensor of FIGS. 10A-10D, including a pin block assembly with a pin block cover removed.

As shown in FIGS. 10C-10E, the substrate 410 includes a through hole 415 extending through the distal surface 410b and the lateral region 412b of the proximal surface 410a. The through hole 415 is aligned with the pin block assembly 440 which is secured to the lateral region 412b of the proximal surface 410a of the substrate 410. Optionally, in some embodiments, as shown for example, in FIG. 10C, a hole 417 is defined in the distal surface 410b and extends at least partially into the substrate 410, in a location symmetrically opposed to through hole 415, to equalize stresses on the substrate 410 during flexing of the substrate 410.

As shown in FIG. 10D, sensing elements "Se" are bonded to the distal surface 410b of the substrate 410. As specifically shown in FIG. 10B, the distal plate 420 includes a substantially planar end wall 422 and a proximally facing flange 424 extending around the end wall 422, such that when the distal plate 420 is mounted on the distal surface 410b of the substrate 410 a cavity or recess 411 (shown in phantom) is defined between the end wall 422 of the distal plate 420 and the distal surface 410b of the substrate 410, providing space and clearance for the sensing elements "Se" and associated components (not shown). The distal plate 420 is secured to the distal surface 410b of the substrate 410 in a fluid tight manner. In embodiments, the distal plate 420 is welded, for example, by laser or electronic beam welding, to the distal surface 410b of the substrate 410 around the entirety of an outer perimeter "Po" and the entirety of an inner perimeter "Pi" of the distal plate 420 to form a hermetic seal to protect the sensing elements "Se" and associated components from the external environment, such as, for example, during sterilizing and/or autoclaving processes. The distal plate 420 has a minimal thickness so as to bend and to allow for a responsive signal from the substrate 410 upon loading. In embodiments, the distal plate 420 has a thickness of about 0.004 inches to about 0.02 inches, and in some embodiments, about 0.01 inches.

Figure 11B:
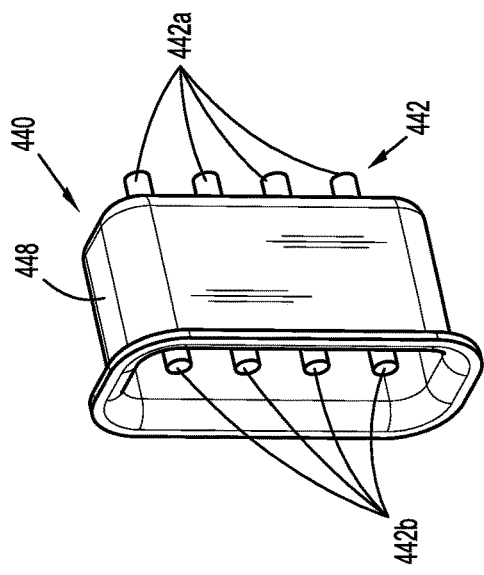
FIGS. 11A and 11B are perspective views of a pin block assembly of the force sensor of FIGS. 10A and 10B.
Figure 11A:
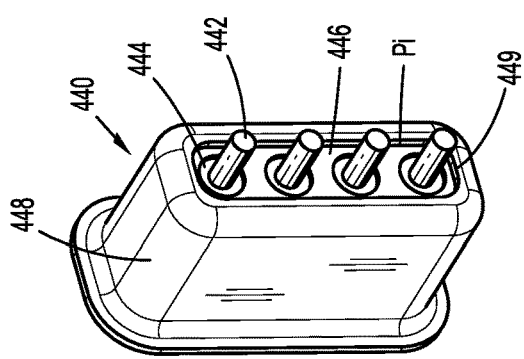

As shown in FIGS. 11A and 11B, in conjunction with FIGS. 10A and 10E, the pin block assembly 440 includes a plurality of conductive pins 442, with each pin 442 extending through a glass substrate or seal 444 disposed within an opening 445 of a pin block housing 446 which is housed within a pin block cover 448. The pin block cover 448 includes a proximal opening 449 through which the plurality of conductive pins 442 extend. The pin block housing 446 and the pin block cover 448 are secured together, e.g., by welding, along the entire inner perimeter "Pi" of the proximal opening 449 of the pin block cover 448. Each conductive pin 442 includes a proximal portion 442a, a distal portion 442b, and a central portion 442c (shown in phantom) disposed therebetween. The central portion 442c is disposed within the glass substrate 444 and the proximal and distal portions 442a, 442b extend proximally and distally, respectively, therefrom.

The pin block housing 346 includes a plurality of openings 445 defined therethrough that correspond to the desired number of conductive pins 442. The conductive pins 442 are sealed with the pin block housing 446 by the glass substrates 444 as described, for example, above with regard to pin block assembly 340. As shown in FIG. 11B, the distal portions 442b of the conductive pins 442 are disposed within the pin block cover 448, and the proximal portions 442a of the plurality of conductive pins 442 extend proximally out through the pin block cover 448.

Figure 12:
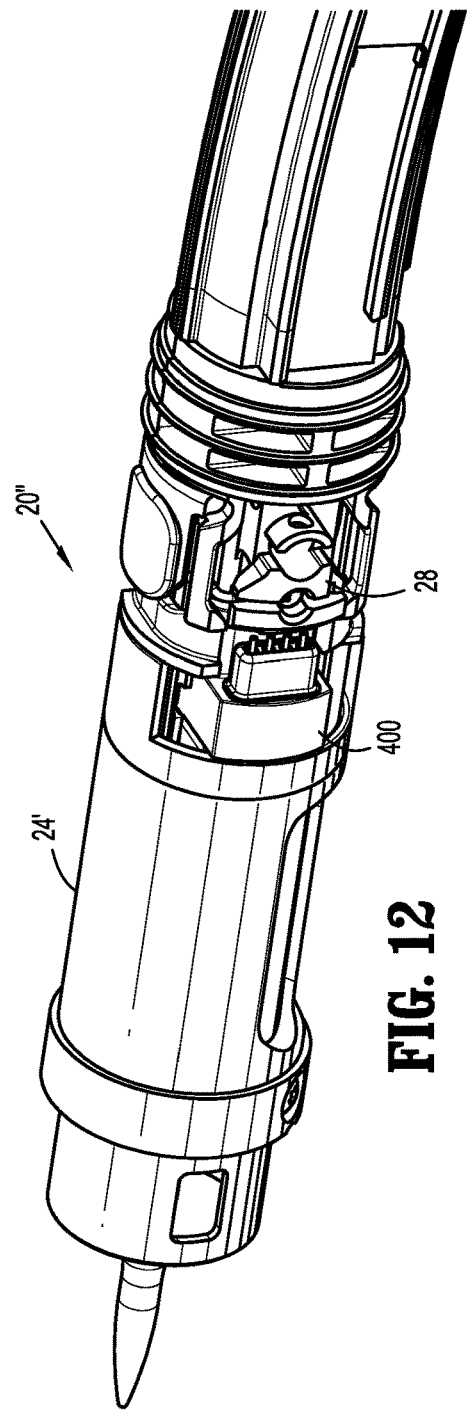
FIG. 12 is a perspective view of a distal end portion of an adapter assembly of a surgical device including the force sensor of FIGS. 10A-10E, with an outer sleeve of the adapter assembly removed therefrom.

As shown in FIG. 10A, the pin block cover 448 is secured (e.g., by welding) to the lateral region 412b of the proximal surface 410a of the substrate 410 around the entirety of an outer perimeter "Pp" of the pin block cover 448, such that the distal portions 442b of the plurality of conductive pins 442 are hermetically sealed within the pin block assembly 440. Wires (not shown) are connected (e.g., soldered) to the sensing elements "Se" (FIG. 10D) of the substrate 410 in a bridge configuration (e.g., a Wheatstone bridge), passed through the through hole 415, and soldered to the distal ends 442b of the plurality of conductive pins 442 disposed within the pin block cover 448 so that electrical signals may exit the substrate 410 in order to supply power and read force responses from the force sensor 400, while allowing the internal wires and electronics to be protected from the outside environment. Additionally, the hermetic sealing of the pin block assembly 440 and distal plate 420 to the substrate 410, as well as the use of glass seals 444 within the pin block assembly 440, allows the force sensor 410 to withstand harsh environments (e.g., autowashing and autoclaving) so that an adapter assembly 20", such as that shown in FIG. 12, can be cleaned and/or sterilized for multiple uses.

Turning to FIGS. 13A-13D, another embodiment of a force sensor 400' is shown. The force sensor 400' is similar to force sensor 400, and therefore will be described with respect to the differences therebetween. The force sensor 400' includes a substrate 410', a distal or first plate 420', and a pin block assembly 440.

The substrate 410' includes a proximal surface 410a and a distal surface 410b'. The distal surface 410b' is substantially planar, and defines a distal or first recess 411' therein. The first recess 411' is defined in one side of a central aperture 401' of the substrate 410', however, it should be understood that a second recess may be defined in the other side of the central aperture 401' in a location symmetrically opposed to the first recess 411'. A through hole 415' extends between a back wall 414a of the first recess 411' and a lateral region 412b of the proximal surface 410a of the substrate 410'. Sensing elements "Se" (see e.g., FIG. 10D) are secured within the first recess 411' and the distal plate 420' is secured (e.g., welded) to the distal surface 410b' of the substrate 410' around the entire outer perimeter "Po" of the distal plate 420' to form a hermetic seal to protect the sensing elements and associated components from the external environment. Wires (not shown) that are soldered to the sensing elements, are passed through the through hole 415' and secured to conductive pins 442 of the pin block assembly 440, as described above.

Figure 13B:
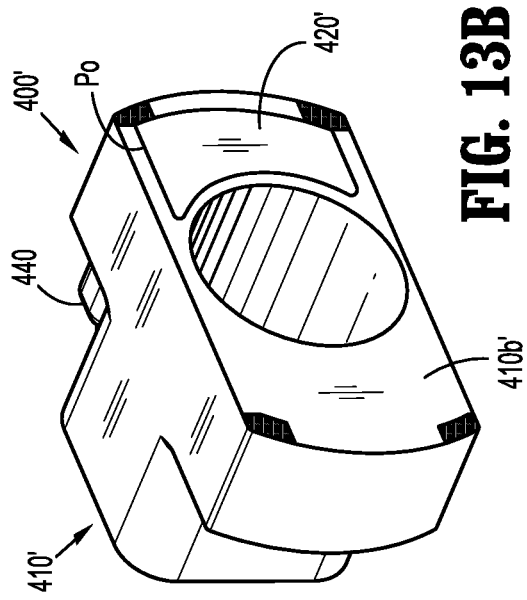
FIGS. 13A and 13B are perspective views of a force sensor in accordance with yet another embodiment of the present disclosure.
Figure 13D:
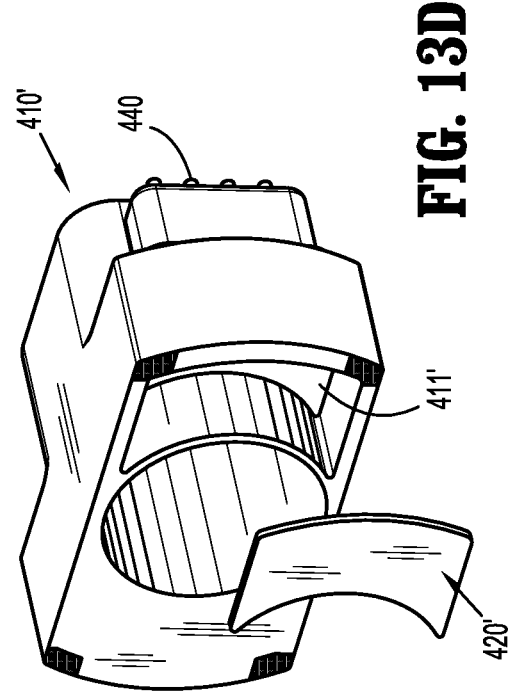
FIG. 13D is a perspective view of the force sensor of FIGS. 13A-13C, with a distal plate separated from the substrate.
Figure 13A:
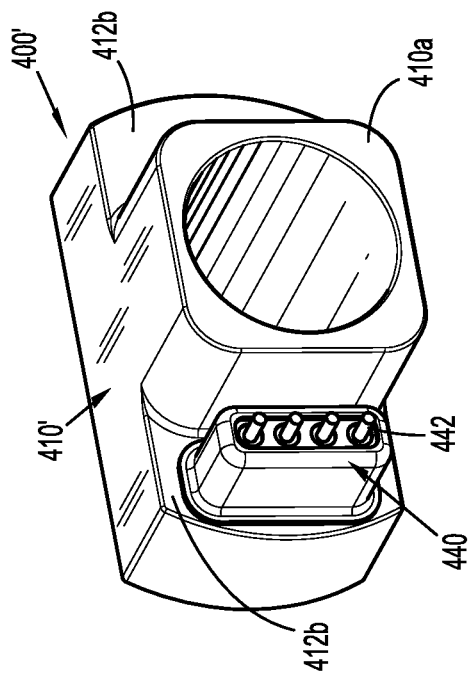
Figure 13C:
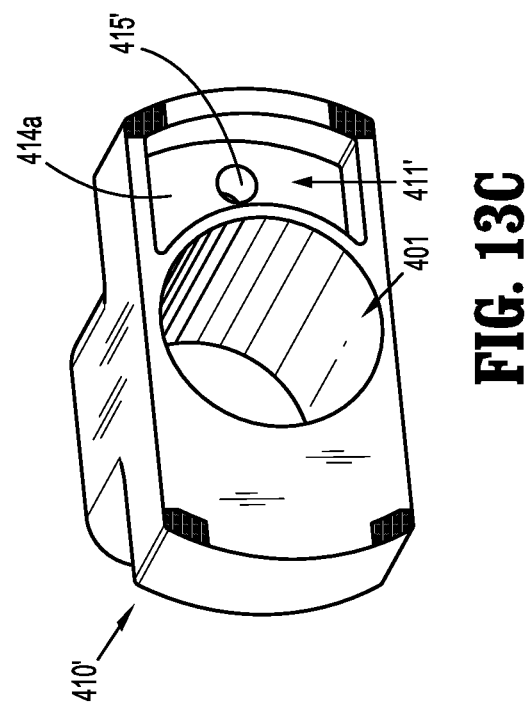
FIG. 13C is a perspective view of the force sensor of FIGS. 13A and 13B, illustrating a substrate thereof.
Figure 13F:
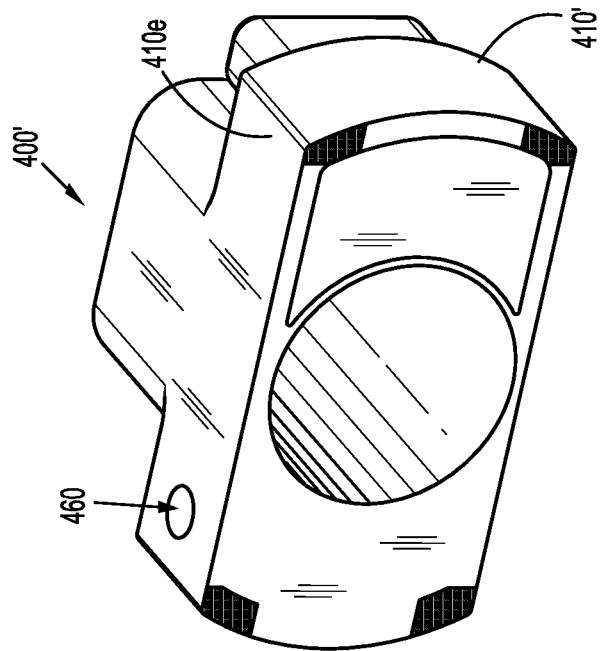
FIGS. 13E and 13F are perspective views of the force sensor of FIGS. 13A-13D including relief features in accordance with embodiments of the present disclosure.
Figure 13E:
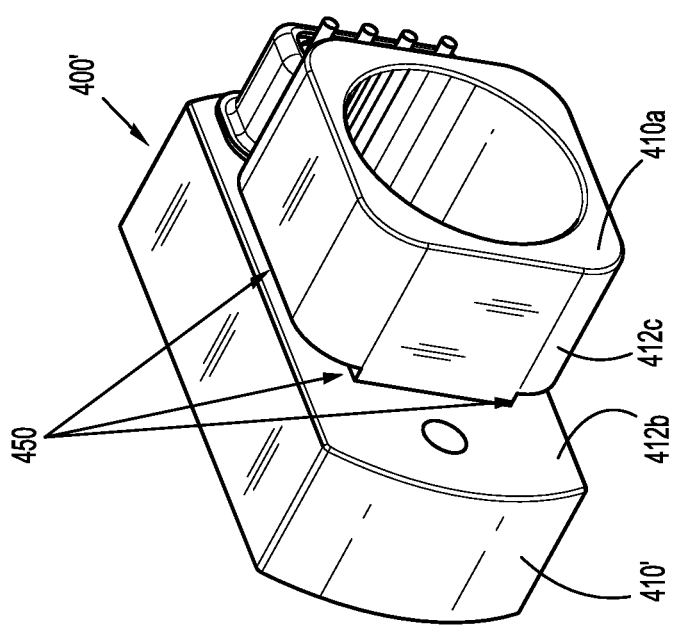
Figure 14B:
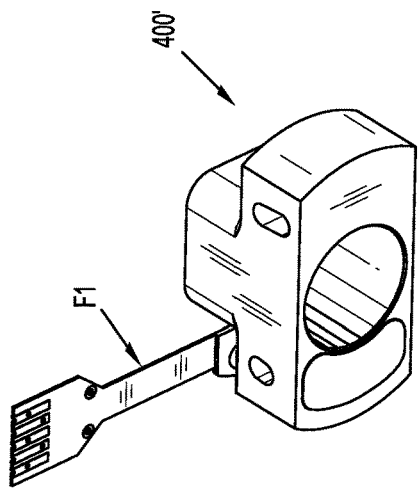
FIGS. 14A and 14B are perspective views of the force sensor of FIGS. 13A-13D including relief features in accordance with an embodiment of the present disclosure, and shown with a sensor flex cable.
Figure 14D:
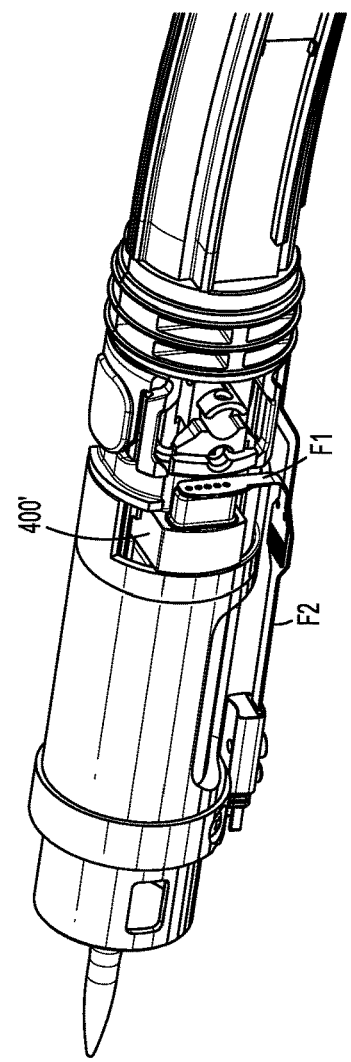
FIG. 14D is a perspective view of a distal portion of an adapter assembly of a surgical device, with some parts removed, including the sensor assembly of FIG. 14C.
Figure 14A:
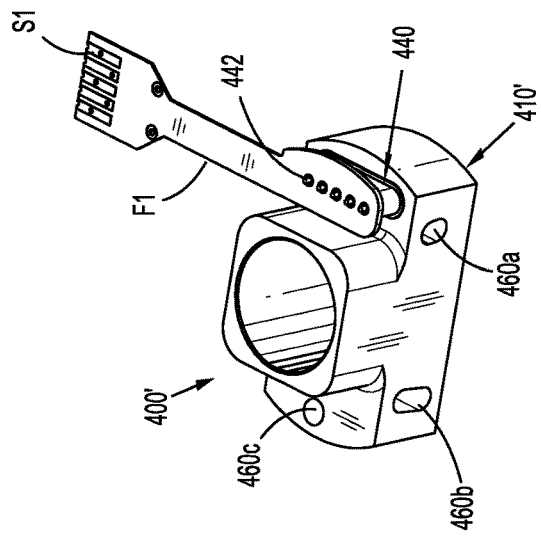
Figure 14C:
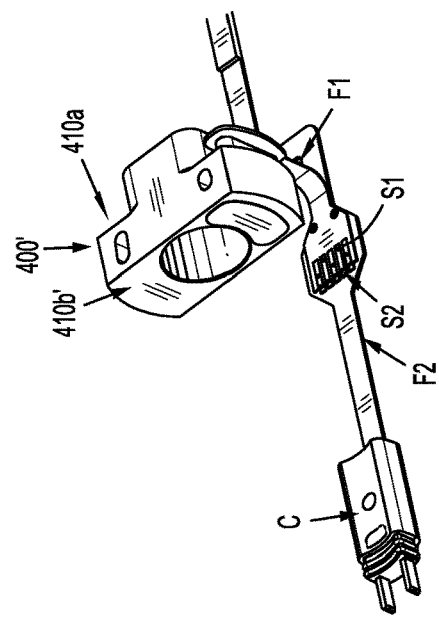
FIG. 14C is a perspective view of a sensor assembly including the force sensor of FIGS. 14A and 14B.
Figure 16B:
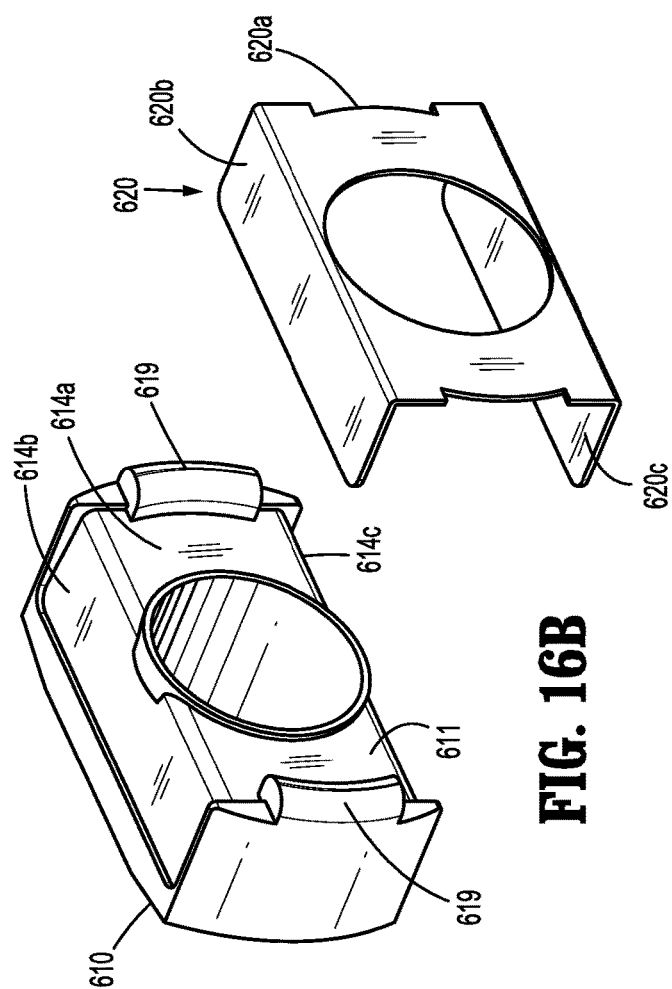
FIG. 16B is a perspective view, with parts separated, of the force sensor of FIG. 16A.
Figure 16D:
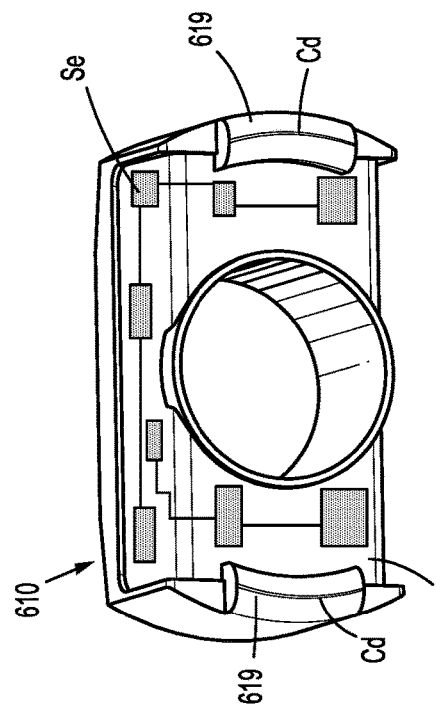
FIGS. 16C and 16D are perspective views of a substrate of the force sensor of FIGS. 16A and 16B.
Figure 16A:
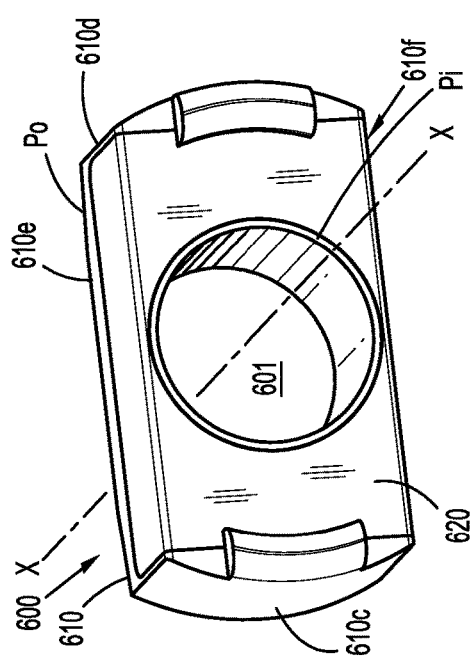
FIG. 16A is a perspective view of a force sensor in accordance with yet another embodiment of the present disclosure.
Figure 16C:
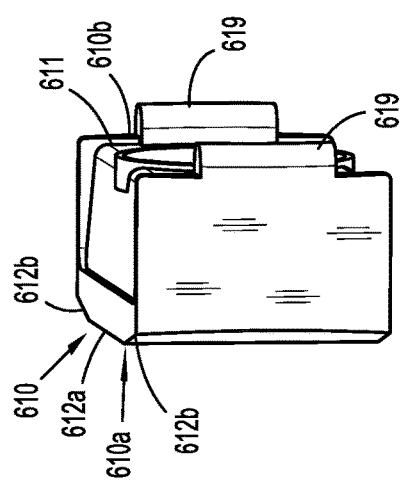

In embodiments in which more elongation (e.g., flex) is desired, the substrate of the force sensors 100, 100', 200, 300, 400, 400' may include one or more relief features to facilitate bending or to reduce stiffness. As shown, for example, in FIG. 13E, a series of relief cuts 450 are formed in the substrate 410' of the force sensor 400' adjacent the lateral region 412b and the intermediate region 412c of the stepped proximal surface 410a. As another example, as shown in FIG. 13F, a hole 460 is defined in a top surface 410e' of the substrate 410' of the force sensor 400'. The relief cuts 450 and/or holes 460 may be formed in a variety of sizes and shapes, such as, but not limited to circular, square, elliptical, trapezoidal, etc., and may be symmetrically positioned about the substrate.

As shown in FIGS. 14A-14D, the force sensor 400', which includes a plurality of relief features or holes 460a-460c defined in the substrate 410', is electrically coupled to a sensor flex cable "F1" via the plurality of conductive pins 442 of the pin block assembly 440. As specifically shown in FIG. 14C, the sensor flex cable "F1" includes solder pads "S1" which are aligned and soldered to solder pads "S2" of an adapter flex cable "F2", the connection of which may be coated with a conformal coating, such as HUMISEAL® UV-40 which is a registered trademark owned by Columbia Chase Corporation, or a flexible resin, such as DOLPHON® CB-1109 PBT which is a registered trademark owned by John C. Dolph Company. The adapter flex cable "F2" extends distally to an electrical connector "C" (see e.g., FIG. 14D) for electrical connection with an end effector 30 (FIG. 1), and also extends proximally to an electrical connector (not shown) for electrical connection with the powered handle assembly 10 (FIG. 1).

While the sensor flex cable "F1" is shown coupled to and extending from the proximal surface 410a of the force sensor 400', it should be understood that the sensor flex cable "F1" may be coupled to a distal surface of a force sensor in embodiments in which a through hole extends through the distal surface, as shown, for example, in FIGS. 6A-6D. It is contemplated that through hole(s) utilized for electrically connecting the sensing elements of the force sensor with the electronics of the surgical device may extend through either the proximal or distal surfaces of the force sensor described herein.

Referring now to FIGS. 15A-15D, a force sensor 500 in accordance with yet another embodiment is shown. The force sensor 100 includes a substrate 510, a first plate set 520, and a second plate 530 bonded to the substrate 510 in a fluid tight manner. A central aperture 501 is defined through the substrate 510 and extends along a central longitudinal axis "X" of the substrate 510. The substrate 510 includes a proximal surface 510a having central and lateral regions 512a, 512b, and a distal surface 510b having a distally extending flange 513 extending around the central aperture 501 of the substrate 510. The proximal and distal surfaces 510a, 510b are load bearing surfaces, as described above with regard to force sensor 100, that allow the substrate 510 to flex when loaded by the surgical device 1 (FIG. 1).

The distal surface 510b includes a distal recess 511 defined therein. The distal recess 511 is a stepped recess including proximal recess portions 511a disposed on opposed sides of the central aperture 501 and a distal recess portion 511b. Proximal recessed lips 518a are defined between the proximal and distal recess portions 511a, 511b, and a distal recessed lip 518b is defined between the distal recess portion 511b and the distal surface 510b. Sensing elements "Se" (see e.g., FIG. 7D) are positioned in at least one of the proximal recess portions 511a and the first plate set 520 is disposed over the proximal recess portions 511a in abutting relation with the proximal recessed lips 518a and secured thereto (e.g., by welding). In embodiments, additional clearance may be provided between the proximal recess portions 511a to allow for tracing wires to extend between the proximal recess portions 511a. Each plate of the first plate set 520 includes a cut-out 522 defined therethrough that is open for the passage of wires (not shown) therethrough. In embodiments, the cut-out 522 is disposed in an outer perimeter of each plate of the first plate set 522, however, it should be understood that the cut-out 522 may be defined in any portion of the plates of the first plate set 522.

Additional electronic components may be placed on the distal facing surfaces of the plates of the first plate set 522, and the second plate 530 is positioned over the distal recess portion 511b in abutting relation with the distal recessed lip 518b so that it is flush with the distal surface 510b of the substrate 510. The second plate 530 is secured thereto (e.g., by welding around the entirety of an outer perimeter "Po" and an inner perimeter "Pi" of the second plate 530) to form a hermetic seal to protect the sensing elements "Se" and associated components from the external environment. While the second plate 530 is shown and described as being received within the distal recessed lip 518b, it should be understood that the second plate 530 may be mounted to the distal surface 510b as shown and described, for example, with respect to the second plate 130 of the force sensor 110. The second plate 530 includes a through hole 532 disposed therethrough to allow for the passage of wires and/or cables (not shown) therethrough. The through hole 532 may include a sealant (not shown) to form a seal, as described above, for example, with respect to the through hole 115 of substrate 110.

Referring now to FIGS. 16A-16D, a force sensor 600 is shown in accordance with yet another embodiment of the present disclosure. The force sensor 600 includes a substrate 610 having a central aperture 601 extending therethrough along a central longitudinal axis "X," and a cap or plate 620 configured to mate with substrate 610. The substrate 610 includes a proximal surface 610a, a distal surface 610b, a first side surface 610c, a second side surface 610d, a top surface 610e, and a bottom surface 610f. The proximal surface 610a includes central and lateral regions 612a, 612b that are substantially identical to, for example, the proximal surface 110a of force sensor 100. Load bearing tabs 619 extend distally from opposed sides of the distal surface 610b which may include lines of contact which act as distal load contact areas "Cd." In embodiments, the load bearing tabs 619 are full radius load bearing tabs, and in some embodiments, the load bearing tabs 619 are linear tabs with a full radius of contact. The longitudinal length of the load bearing tabs 619 may vary, for example, to increase the thickness of the substrate 610 to increase the strength of the force sensor 600.

The substrate 610 includes a single continuous recess 611 defined in at least two surfaces of the substrate 610, and in embodiments, in at least three surfaces of the substrate 610. As shown, the recess 611 is defined in the distal surface 610b, the top surface 610e, and the bottom surface 610f of the substrate 610. The recess 611 provides increased surface area for bonding of sensing elements "Se" thereto. In embodiments, the increased surface area allows the sensing elements "Se" to be placed on smaller substrates. As specifically shown in FIG. 16B, the recess 611 include a substantially planar back wall 614a and angled top and bottom walls 614b, 614c that taper proximally. It should be understood that the walls of the recess may be angled or planar depending on the desired characteristics of the force sensor 600.

The cap 620 is configured and dimensioned to cover the recess 611. As shown, the cap 620 includes a back side 620a corresponding with the distal surface 610b of the substrate, a top side 620b corresponding with the top surface 610e of the substrate 610, and a bottom side 620c corresponding with the bottom surface 610f of the substrate 610. The cap 620 is positioned on the substrate 610 such that the sides thereof match the surfaces of the substrate 610 and lie flush therewith. As shown, the back side 620a lies flush with the distal surfaces 610b of the substrate 610, the top side 620b lies flush with the top surface 610e of the substrate 610, and the bottom side 620c lies flush with the bottom surface 610f of the substrate 610. The cap 620 is sealed to the substrate 610 in a fluid tight manner by, for example, welding the cap 620 around an entire outer perimeter "Po" and an entire inner perimeter "Pi" of the cap 620 to the substrate 610. A through hole (not shown) may be provided in the cap 620, in a similar manner as through hole 532 of force sensor 500, or through the substrate 610 in a similar manner as through hole 415 of force sensor 400, for example.

The surgical device is used, for example, in an anastomosis procedure to effect joining of two tubular or hollow tissue sections (e.g., intestinal section) together. Generally, referring again to FIG. 1, the anvil assembly 34 may be applied to the operative site either through a surgical incision or transanally and positioned within a first intestinal section (not shown) and secured temporarily thereto (e.g., by a purse string suture), and the loading unit 32 and outer sleeve 22 of the adapter assembly 20 may be inserted transanally into a second intestinal section (not shown) and secured temporarily thereto. Thereafter, a clinician maneuvers the anvil assembly 34 until the proximal end of the anvil rod 34b is inserted into the distal end of the adapter assembly 20, wherein mounting structure (not shown) within the distal end of adapter assembly 20 engages anvil rod 34b to effect mounting. The anvil assembly 34 and the loading unit 32 are then approximated to approximate the first and second intestinal sections. Surgical device 1 is then fired, and a knife (not shown) cuts the portion of tissue disposed radially inward of the knife, to complete the anastomosis.

The force sensors of the present disclosure may be utilized to enhance the anastomosis procedure by controlling a function of the surgical device. For example, the force sensor may be used to control the force and/or rate of compression of tissue. If tissue is compressed too rapidly, it may become bruised, torn, damaged, etc. during such compression. Without being bound to any particular theory, it is believed that maintaining a constant force of compression on the tissue of, for example, around 150 pounds, provides a steady yet rapid compression of tissue until the optimal staple gap is achieved for performing stapling and cutting functions. The force sensors may be utilized to first read the force to compress the tissue. Once compressed, the force sensor may also monitor the stapling function. Such monitoring allows for the programming of the stapling function. In embodiments, the surgical device is programmed to deliver a preset load depending on the anvil selected. For example, a smaller anvil, e.g., a 21 mm anvil, requires a lower force than a larger anvil, e.g., a 33 mm anvil. In embodiments, the cutting function may be controlled to stop at a predetermined force. This allows for the electronics and software to control such functions eliminating the need for tight mechanical stops.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. For example, the force sensors of the present disclosure may be utilized in other surgical devices, such as robotic or powered surgical devices/instruments, having a force sensor disposed therein and/or that are subject to sterilization procedures (e.g., autoclaving and/or autowashing). Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A force sensor comprising:
a substrate including a central aperture extending along a longitudinal axis of the substrate, the substrate having a proximal surface, a distal surface, a first side surface, a second side surface, a top surface, and a bottom surface, at least one of the distal surface, the first side surface, the second side surface, the top surface, or the bottom surface including a recess defined therein;
a plurality of sensing elements disposed within the recess; and
a plate disposed over the recess and mounted to the substrate to hermetically seal the plurality of sensing elements within the substrate.

2. The force sensor according to claim 1, wherein the recess is a first recess defined in the first side surface of the substrate, the first recess including a back wall, a proximal-facing wall, a distal-facing wall, a top wall, and a bottom wall.

3. The force sensor according to claim 2, wherein the back wall, the proximal-facing wall, the distal-facing wall, the top wall, and the bottom wall are all substantially planar.

4. The force sensor according to claim 2, wherein the back wall is angled with respect to the longitudinal axis of the substrate, and the proximal-facing and distal-facing walls are angled with respect to the back wall.

5. The force sensor according to claim 2, wherein the plate is welded to the first side surface of the substrate.

6. The force sensor according to claim 2, wherein the first side surface includes a recessed lip defined around an inner perimeter thereof, and the plate is received within the recessed lip.

7. The force sensor according to claim 2, wherein a second recess is defined in the second side surface of the substrate.

8. The force sensor according to claim 1, wherein a through hole extends through a wall of the recess and the proximal surface of the substrate.

9. The force sensor according to claim 8, wherein at least one wire is coupled to the plurality of sensing elements disposed within the recess and extends through the through hole.

10. The force sensor according to claim 9, wherein a sealant is disposed within the through hole filling a space defined between an outer diameter of the wire and an inner diameter of the through hole.

11. The force sensor according to claim 8, wherein a pin block assembly is mounted to the substrate and in communication with the through hole of the substrate.

12. The force sensor according to claim 11, wherein the pin block assembly includes a plurality of conductive pins, a plurality of glass seals, and a pin block housing including a plurality of openings, each pin of the plurality of conductive pins extending through a glass seal of the plurality of glass seals which is disposed within an opening of the plurality of openings of the pin block housing.

13. The force sensor according to claim 12, wherein the pin block housing is disposed within the through hole of the substrate.

14. The force sensor according to claim 13, wherein a distal portion of each pin of the plurality of pins is disposed within the recess of the substrate, and a proximal portion of each pin of the plurality of pins is disposed outside of the substrate.

15. The force sensor according to claim 12, wherein the pin block housing of the pin block assembly is disposed within a pin block cover, and the pin block cover is mounted to the substrate and in communication with the through hole of the substrate.

16. The force sensor according to claim 15, wherein a distal portion of each pin of the plurality of pins is disposed within the pin block cover, and a proximal portion of each pin of the plurality of pins extends through the pin block cover.

17. The force sensor according to claim 11, wherein the pin block assembly is welded to the substrate.

18. The force sensor according to claim 1, wherein walls sections of the substrate that define the central aperture are angled with respect to the longitudinal axis of the substrate.

19. The force sensor according to claim 1, wherein the recess is a distal recess defined in the distal surface of the substrate.

20. The force sensor according to claim 1, wherein the recess is defined in at least two of the distal surface, the first side surface, the second side surface, the top surface, or the bottom surface of the substrate.

* * * * *